(12) United States Patent
Pokorney et al.

(10) Patent No.: US 10,518,066 B2
(45) Date of Patent: Dec. 31, 2019

(54) MEDICAL GUIDEWIRES FOR TORTUOUS VESSELS

(71) Applicant: MIVI Neuroscience, Inc., Eden Prairie, MN (US)

(72) Inventors: James Pokorney, Northfield, MN (US); Matthew F. Ogle, Edina, MN (US)

(73) Assignee: MIVI Neuroscience, Inc., Eden Prairie, MN (US)

( * ) Notice: Subject to any disclaimer, the term of this patent is extended or adjusted under 35 U.S.C. 154(b) by 519 days.

(21) Appl. No.: 14/593,766

(22) Filed: Jan. 9, 2015

(65) Prior Publication Data
US 2016/0199620 A1    Jul. 14, 2016

(51) Int. Cl.
*A61M 25/09*    (2006.01)
*A61M 25/01*    (2006.01)

(52) U.S. Cl.
CPC ...... *A61M 25/09* (2013.01); *A61M 25/09033* (2013.01); *A61M 25/09041* (2013.01); *A61M 25/0136* (2013.01); *A61M 25/0147* (2013.01); *A61M 2025/09083* (2013.01); *A61M 2025/09166* (2013.01)

(58) Field of Classification Search
CPC .................................................. A61M 25/09
See application file for complete search history.

(56) References Cited

U.S. PATENT DOCUMENTS

| | | | | |
|---|---|---|---|---|
| 4,832,047 A | * | 5/1989 | Sepetka | A61M 25/09033 600/434 |
| 5,234,003 A | * | 8/1993 | Hall | A61M 25/09 600/434 |
| 5,392,778 A | | 2/1995 | Horzewski | |
| 5,673,707 A | * | 10/1997 | Chandrasekaran | A61M 25/09 600/434 |
| 6,652,472 B2 | | 11/2003 | Jafari et al. | |
| 6,666,829 B2 | | 12/2003 | Cornish et al. | |
| 7,044,921 B2 | | 5/2006 | Asmus et al. | |
| 7,892,187 B2 | | 2/2011 | Murayama et al. | |
| 7,988,705 B2 | | 8/2011 | Galdonik et al. | |
| 8,070,694 B2 | | 12/2011 | Galdonik et al. | |
| 8,092,483 B2 | | 1/2012 | Galdonik et al. | |
| 8,708,933 B2 | | 4/2014 | Cornish et al. | |
| 8,814,892 B2 | | 8/2014 | Galdonik et al. | |

(Continued)

FOREIGN PATENT DOCUMENTS

WO    02-36194 A2    5/2002

OTHER PUBLICATIONS

International Search Report and Written Opinion from co-pending application, PCT/US2016/12723, dated Aug. 8, 2016 (11 pages).

(Continued)

*Primary Examiner* — Sean P Dougherty
(74) *Attorney, Agent, or Firm* — Christensen, Fonder, Dardi & Herbert PLLC; Peter S. Dardi; Andrew Auderieth

(57) ABSTRACT

Three groups of guidewire embodiments are described with particularly suitable structures for navigating circuitous vessels, especially blood vessels of the brain. Some of the guidewires have a hyperbolic taper that provides desired flexibility. In some embodiments, an integrated guide structure provides for extension in the blood vessel of a corewire to provide for extended reach of the guidewire. In further embodiments, the guidewire has a flexible tip that can be guided directly by the flow in the vessel.

13 Claims, 11 Drawing Sheets

(56) References Cited

U.S. PATENT DOCUMENTS

| | | |
|---|---|---|
| 8,845,553 B2 | 9/2014 | Brown |
| 2004/0064130 A1* | 4/2004 | Carter ............... A61M 25/0045 |
| | | 604/523 |
| 2005/0209631 A1 | 9/2005 | Galdonik et al. |
| 2006/0006649 A1 | 1/2006 | Galdonik et al. |
| 2006/0058836 A1 | 3/2006 | Bose et al. |
| 2010/0010476 A1 | 1/2010 | Galdonik et al. |
| 2010/0063480 A1* | 3/2010 | Shireman .......... A61M 25/0054 |
| | | 604/528 |
| 2010/0228150 A1 | 9/2010 | Zimmerman et al. |
| 2010/0256600 A1 | 10/2010 | Ferrera |
| 2011/0230840 A1* | 9/2011 | Cornish ................ A61M 25/09 |
| | | 604/164.13 |
| 2011/0230859 A1 | 9/2011 | Galdonik et al. |
| 2012/0127563 A1* | 5/2012 | Farmer .................... G02B 6/14 |
| | | 359/341.3 |
| 2012/0262781 A1* | 10/2012 | Price ....................... G02B 6/14 |
| | | 359/341.3 |

OTHER PUBLICATIONS

European Search Report from co-pending European application PCT/US2016/012723, dated Sep. 4, 2018 (7 pages).

* cited by examiner

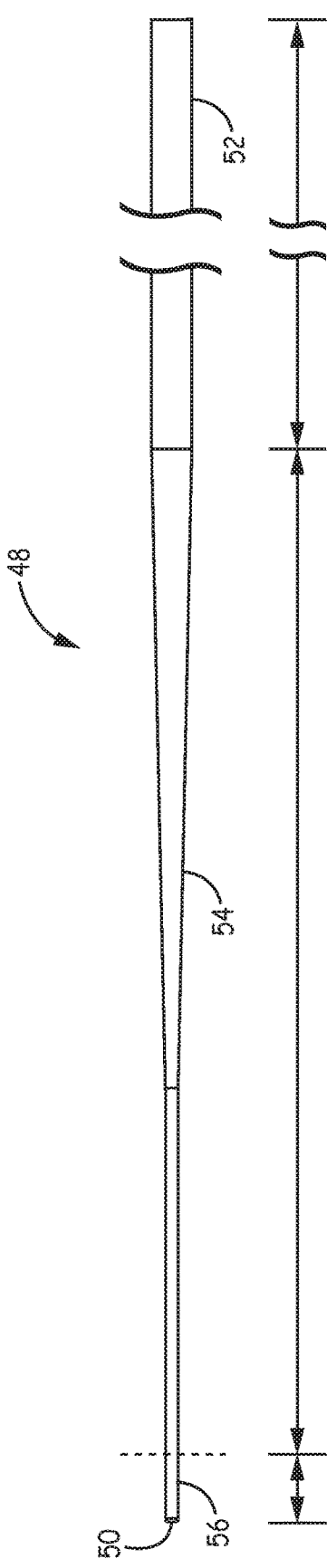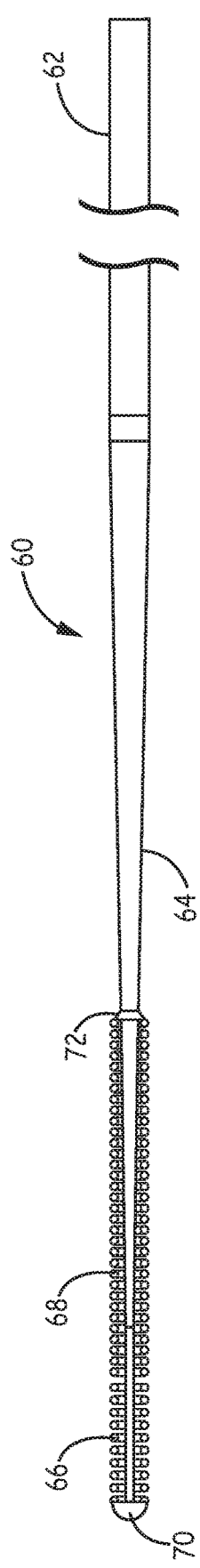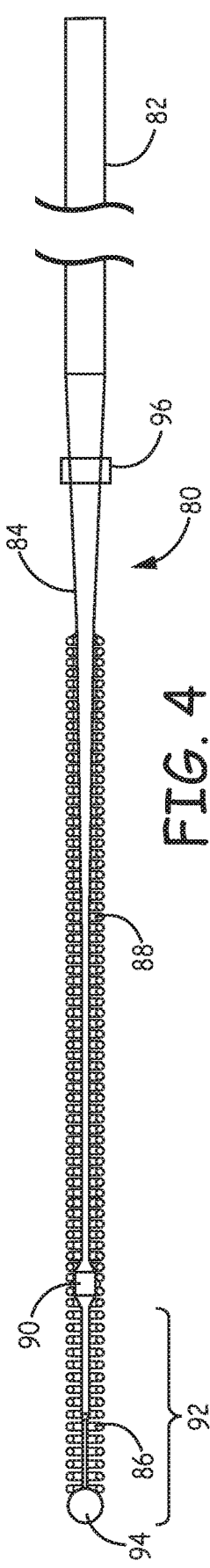

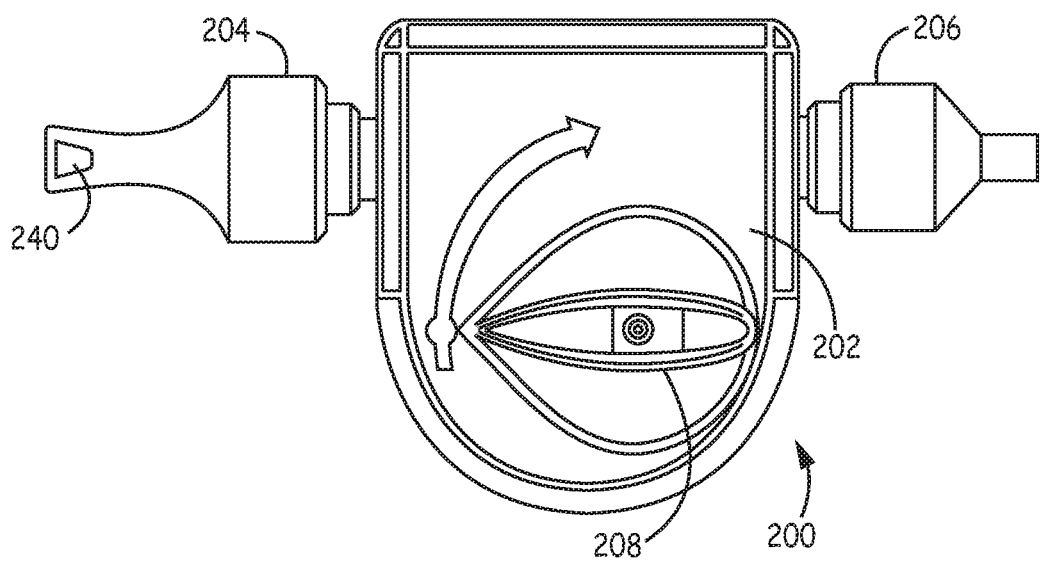
FIG. 12 - Prior Art
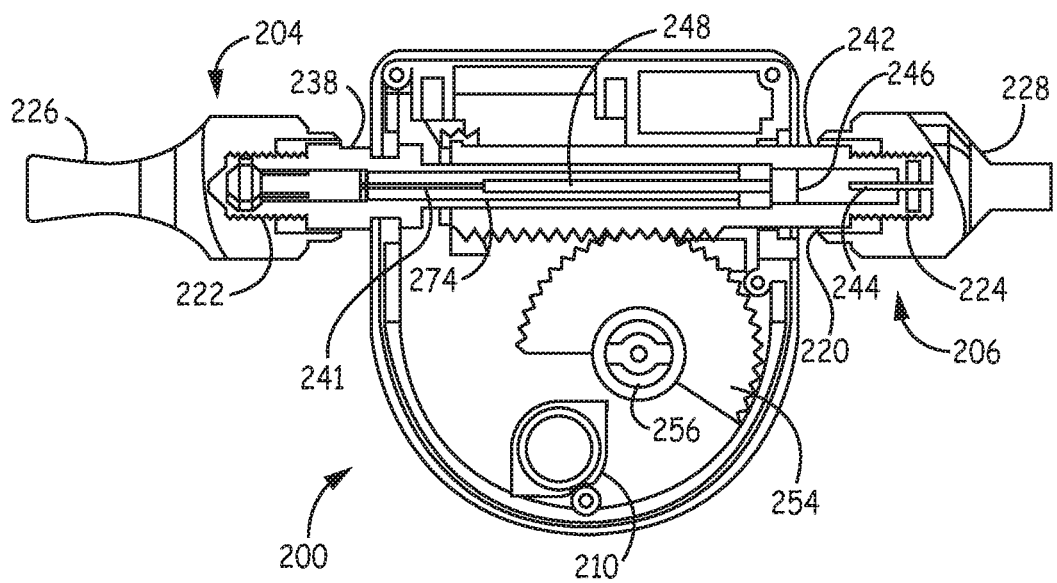
FIG. 13 - Prior Art

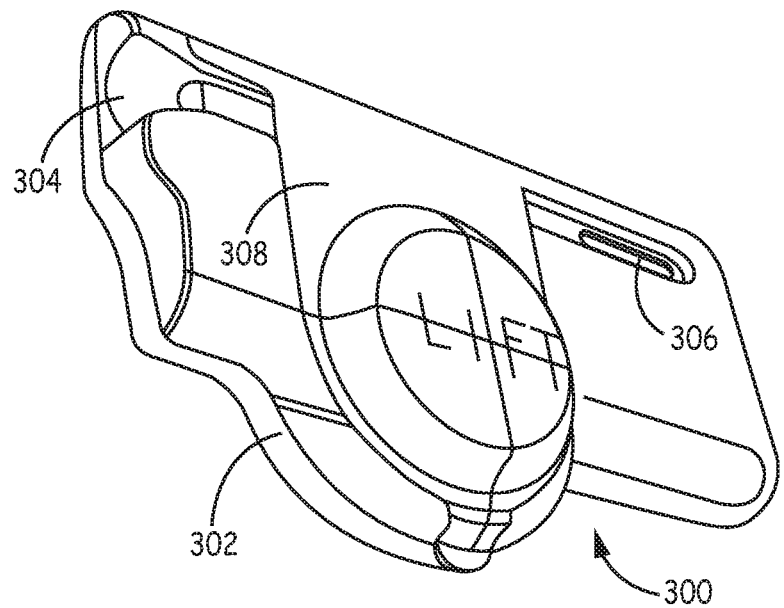
FIG. 14 - Prior Art
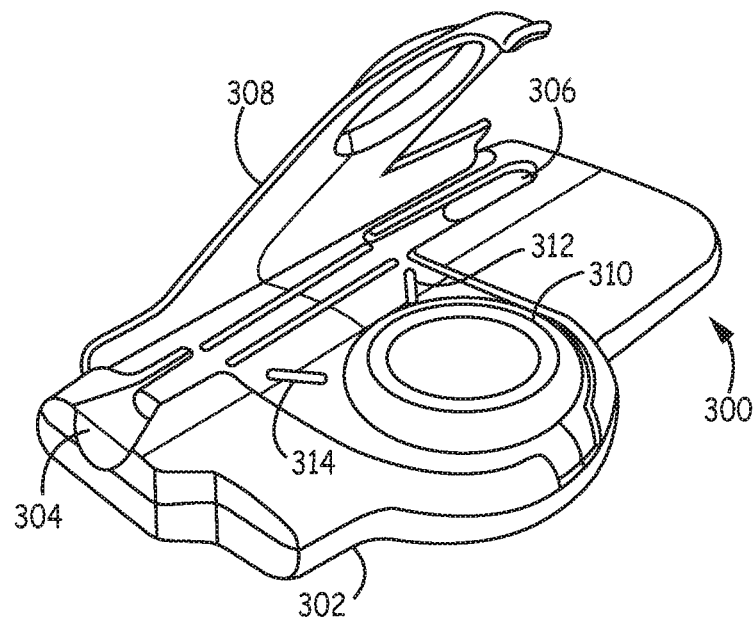
FIG. 15 - Prior Art

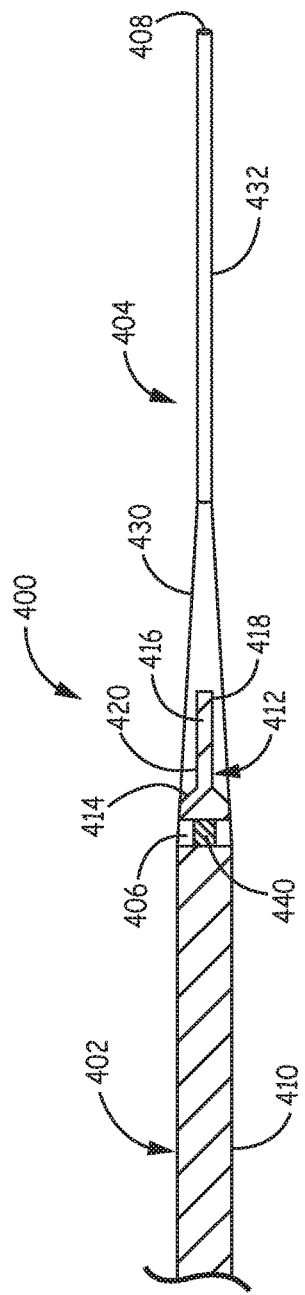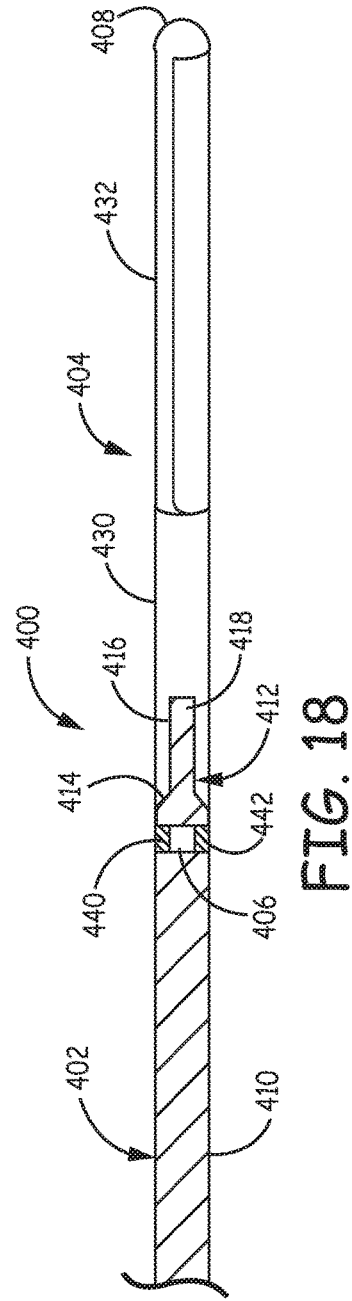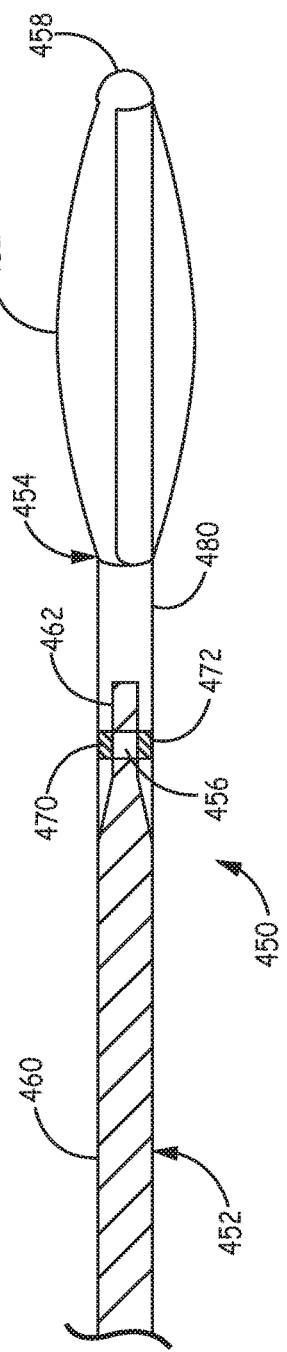

MEDICAL GUIDEWIRES FOR TORTUOUS VESSELS

FIELD OF THE INVENTION

The invention relates to medical guidewire designs suitable for use in bodily vessels of a patient that have tortuous paths. The invention further relates to use of the medical guidewires to assist with medical procedures in the vessels, such as procedures in cerebral blood vessels.

BACKGROUND OF THE INVENTION

Procedures in blood vessels of the brain are gaining interest as an approach for ameliorating acute stroke events or other interventions in blood vessels in the brain. Blood vessels in the brain follow particularly tortuous paths which can increase the difficulty of reaching target locations in these vessels. Other vessels in a patient can also follow winding paths that increase the difficulty of reaching target locations.

Guidewires are frequently used to access a location within a vessel, such as blood vessels, of a patient. The guidewire can be placed during a relatively early portion of a procedure, and a further intervention device can then be guided over the guidewire to reach a target location. Once a further device is in place, the guidewire may or may not be removed for the remainder of the procedure.

SUMMARY OF THE INVENTION

In a first aspect, the invention pertains to an integrated guiding device comprising a corewire and an overtube. The overtube has a lumen and the corewire extends through the lumen of the overtube the corewire and the overtube comprising an indentation. The corewire comprises a flattened section along the distal half of the corewire. A fraction of the lateral extent of the flattened section of the corewire is aligned with indentation in the overtube. The flattened section and indentation provide for torque coupling of the corewire and overtube and a defined amount of lateral motion of the corewire relative to the overtube. The corewire can extend from a distal end of the overtube in a configuration with the overtube drawn in a proximal direction relative to the corewire to the extent provided by the aligned indentation of the overtube interfacing with the flattened section of the corewire, and generally the portion of the corewire extending from the overtube is unattached to the overtube. In some embodiments, the corewire extends at least 2 centimeters from the distal end of the overtube. The corewire can be drawn in a proximal direction relative to the corewire to the extent provided by the aligned indentation of the overtube. The indentation interfaces with the flattened section of the corewire. In some embodiments, the extent of lateral motion of the corewire relative to the overtube is at least about 1 centimeter based on the constraints provided by the aligned indentation of the overtube interfacing with the flattened section of the corewire.

In a second aspect, the invention pertains to a method for positioning a device for performing a therapeutic procedure in the vasculature of a patient. The method comprises extending a corewire relative to an overtube of an integrated guide structure to extend the distal reach of the device in a vessel and guiding a therapeutic treatment device over the integrated guide structure to a treatment position at least a portion of which extends beyond the distal end of the overtube.

In another aspect, the invention pertains to a guidewire comprising a solid wire of a biocompatible metal. The guidewire has a length from about 90 cm to about 300 cm with a proximal diameter from about 0.0075 inches (in) about 0.03 in. The guidewire comprises an approximately hyperbolic taper along the distal third of the guidewire length forming a reduced diameter of the wire wherein the hyperbolic taper has a length form about 10 cm to about 60 cm.

In another aspect, the invention pertains to a guidewire comprising a metal wire having a length from about 10 cm to about 400 cm, a proximal diameter from about 0.05 mm to about 1.5 mm, and a distal polymer tip. The distal polymer tip has a flexible flattened section extending from the metal shaft. In some embodiments, the polymer tip can comprise a radiopaque element at or near the distal end.

In another aspect, the invention pertains to a method comprising steering a guidewire within a blood vessel toward a selected branch. The guidewire comprises a distal polymer tip having a flattened section. The method comprises orienting a guidewire such that flow to the branch vessel steers the distal tip toward the selected branch

BRIEF DESCRIPTION OF THE DRAWINGS

FIG. 1 is a side view of an embodiment of the guidewire with a hyperbolic taper.

FIG. 3 is a side view of an embodiment of the guidewire with a hyperbolic taper and a distal coil secured with a proximal weld.

FIG. 4 is a side view of an embodiment of the guidewire with a hyperbolic taper and a distal coil and a torque stabilizer.

FIG. 12 is a side plan view of an actuation tool for moving the corewire relative to the overtube to control extension of the distal end of the corewire.

FIG. 13 is a side view of the actuation tool of FIG. 12 with structure removed to expose internal features of the tool.

FIG. 14 is a top perspective view of a second alternative embodiment of an actuation tool in a load configuration.

FIG. 15 is top perspective view of the actuation tool of FIG. 14 in an actuation configuration in which the dial is exposed.

FIG. 17 is a fragmentary side view of a guidewire with a flexible polymer tip in a first orientation.

FIG. 18 is a fragmentary side view of the guidewire of FIG. 17 rotated 90 degrees relative to the view in FIG. 17 displaying a surface suitable to interface with flow in a vessel to orient the tip.

FIG. 19 is a side view of an alternative embodiment of a guidewire with a flexible polymer tip having an unfurled polymer segment with a larger cross sectional area to interface with the flow.

DETAILED DESCRIPTION OF THE INVENTION

Figure 2:
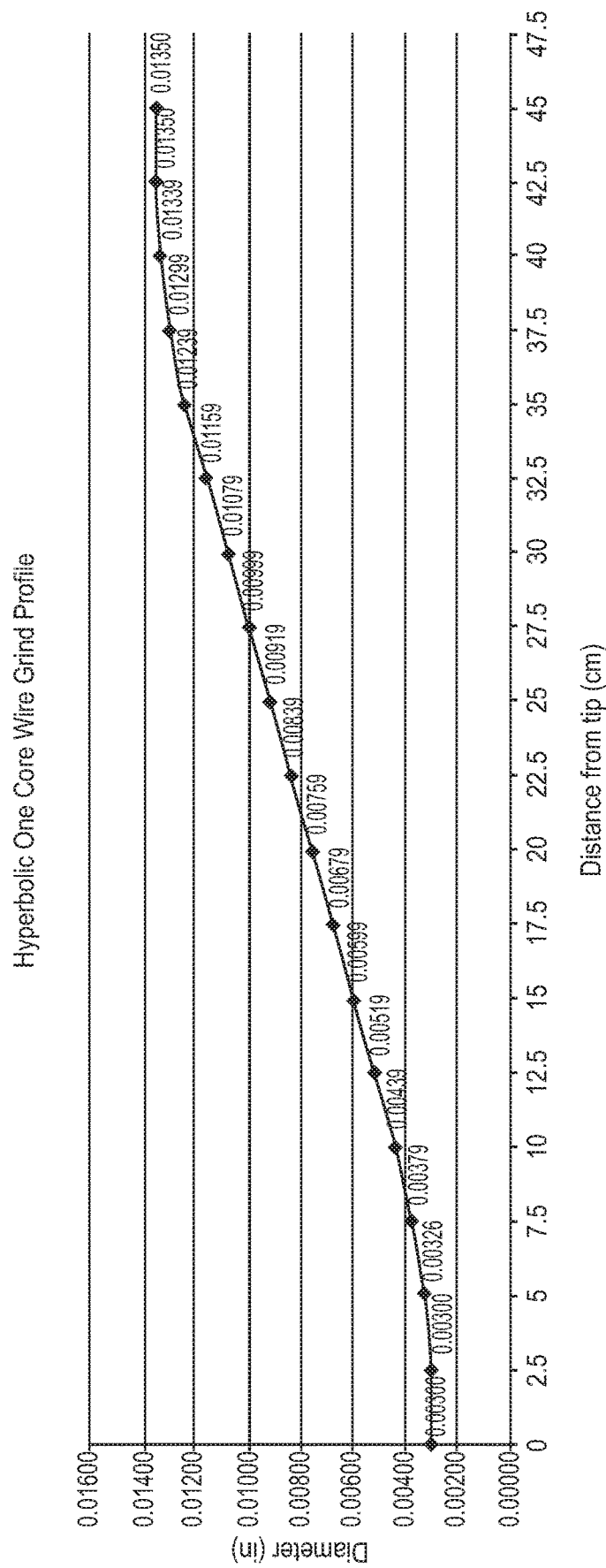
FIG. 2 is a plot of guidewire diameter as a function of the distance from the tip of the guidewire for one representative hyperbolic guidewire grind profile.

Medical guidewires are described with designs to provide for delivery into tortuous vessels with good reach into the vessel so that the guidewires can be used to guide delivery of therapeutic devices to desired locations. In some embodiments, a portion of a solid guidewire element at or near the distal end of the element are provided with a hyperbolic tangent shaped taper that provides a desired gradual increases in flexibility. Coils can be interfaced with the tapered portion of the guidewire to provide desired performance of the guidewires. In additional or alternative embodiments, the guidewires can be formed with a corewire and an overtube in which the core wire can be extended relative to the overtube to provide for additional reach of the guidewire that could not otherwise be reached easily. Guidewires with a corewire and an overtube can be referred to as an integrated guide structure. Thus, as used herein, guidewire refers generally to structures that can have a plurality of structural elements. A torque coupling structure can stabilize the corewire and overtube combination while defining a range of extension achievable through the relative motion of the corewire and overtube. Additional embodiments are described with a very flexible polymer tip portion that is configured to have a flattened section that can be directed or bent by the flow itself. Depending on rotational orientation, much like an airplane wing elevator, the flattened segment can more or less be directed or bent by the flow thereby allowing the user to select the tip to be more straight or more bent at a vessel junction to help select a selected vessel branch. The improved guidewire designs can be particularly useful in tortuous vessels, especially arterial blood vessels in the cerebral vascular downstream from the carotid arteries. The flexible flattened section can be significantly wider than the rest of the guidewire in width and significantly thinner in thickness such that it can be folded or furled around the main axis of the guidewire to facilitate insertion and passage through a microcatheter, guide catheter, and/or Luer connector.

Navigation of cerebral arterial vessels downstream from the carotid arteries are particularly challenging due to a tortuous path of the vessels. Suitable guidewires provide the ability to facilitate delivery into desirable locations on the vasculature. Improvements in the guidewires provide for the skilled delivery of the distal end of the guidewire to more remote locations along a vessel and/or to facilitate the delivery process so that less skill and/or time is involved in the placement of the guidewire. Once the guidewire is in position, a therapeutic device and/or a further structure to facilitate delivery of other devices can be delivered over the guidewire to a selected location for a therapeutic procedure. The guidewire may or may not be removed for the performance of the procedure, but an improvement of the guidewire delivery can provide significant advantages with respect to various procedures.

In general, guidewires can have more flexible distal ends and tips that can be bent to facilitate steering of the guidewire through the vasculature, while a less flexible proximal portions can facilitate pushing of the guidewire from the exterior of the patient. Radiopaque elements at and/or near the distal end of the wire can provide for visualization of the guidewire in the vessel using x-rays during a procedure. Steering of the guidewire can involve rotating the tip to point the tip in a desired direction to advance the wire, and appropriate transmission of torque along the length of the wire provides for the ability to manipulate the portion of the guidewire near the proximal end outside of the patient to rotationally aim the distal tip to a selected vessel branch within the patient. Once aimed, the guidewire can be pushed to advance the guidewire in the vessel. The guidewire should be stiff enough over an appropriate portion of the length of the guidewire to provide for pushing the guidewire at or near the proximal end while advancing the distal end without significant kinking or loss of an appropriate amount of longitudinal forces. All or a significant fraction of the guidewire exterior can be cover or coated with a low friction polymer, such as polytetrafluoroethylene to aid with advancement of the guidewire. At some point, it may be difficult to advance the guidewire further in the vasculature due to loss of transmission of the force to the distal end and/or to friction in the vessel that limits transmission of force to the distal end since it is not desirable to apply excessive amounts of force that could damage some portion of the vessel.

Blood vessels downstream from the carotid arteries, which may be referred to as neuro vessels since they supply blood to the brain, are particularly circuitous and challenging to navigate with guidewires. Thus, neuro guidewires involve design challenges with respect to thinness of the guidewires, torque transmission, tip flexibility and pushability. Several different embodiments are described that address these design challenges. In a first set of embodiments, a hyperbolic shaped taper or grind is introduced to a solid metal guidewire at or near the distal end of the wire and a coil can be placed over at least a portion of the tapered segment to form a distal tip with good flexibility and steerability. The hyperbolic taper can provide a gradual shift in flexibility that can provide good responsiveness of the tip.

In a second set of embodiments, a guidewire is designed as an integrated guide structure having a corewire and an overtube. The corewire and overtube can have one or more torque couplers that couple the rotational motion of the corewire and overtube while providing a defined longitudinal sliding of the corewire relative to the overtube. A distal portion of the overtube can be made more flexible, for example, through applying cuts to the tube, by replacement with a coil and/or through grinding optionally with the placement of a coil over at least a portion of the ground tube. The distal portion of the corewire can have a coil extending over at least a portion of the corewire extending from the end of the overtube. The integrated guide structure embodiments can provide for extension of the guidewire further in the vessel through the sliding of the corewire in a distal direction relative to the overtube once the overtube cannot comfortably be advanced further in the vessel.

In a third set of embodiments, the distal tip of the guidewire is formed of a very flexible polymer structure or combination metal/polymer structure that is designed for orientation driven by the flow. In conventional guidewires, the flexible distal tip is preformed by the user or manufacturer so to allow for rotational manipulation from outside the body to orient the direction of the distal tip. The disadvantage of this design is that the tip is configured with a pre-selected bend even though a different bend or no bend at all would be more advantageous while traversing other regions of the vasculature. In the flow driven designs, the tip is designed to be inserted in a straight, non-bent condition. It is sufficiently flexible that the flow guides the tip, and the shape of the tip can be designed to engage the flow correspondingly. At a branch of the vessel, the tip can be brought relatively near to the entrance to the vessel, and the flow into the vessel naturally guides the tip into the vessel as the guidewire is advanced. Rotation of the guidewire by the user at the proximal end alters the relative engagement of the distal tip In the first set of embodiments, the guidewire is generally formed of a suitable metal with a low friction polymer coating over at least a significant portion of the guidewire surface. The diameter of the wire can be suitable for a neuro vessel application, and suitable materials are described below. Coils can be placed along a portion of the ground section of the wire. To provide for desired responsiveness of the distal tip, the coil can comprise appropriate torque coupling between the coil and the wire, such as one or more connections between the coil and the wire. The hyperbolic grind may or may not extend to the tip of the wire.

With respect to a second set of embodiments, an integrated guide structure has a core wire within an overtube that provide for a greater extension of the distal end of the wire. Integrated guide structures have been used for the deployment and control of functional devices in which the relative movement of the corewire and overtube provide for control of a distal device within a patient based on manipulation outside of the patient. For example, a embolic protection devices has effectively used an integrated guide structure to control the deployment and recovery of a fiber based device, as described in U.S. Pat. No. 8,070,694 to Galdonik et al. (the '694 patent), entitled "Fiber Based Medical Devices and Aspiration Catheters," incorporated herein by reference. In common with the devices in the '694 patent, the present integrated guide structures generally comprise a torque coupling feature between the corewire and the overtube to provide desired control over the corewire extending from the distal top of the device.

In contrast with the procedures described in the '694 patent, in the present procedures, the corewire is generally shifted in a proximal direction relative to the overtube during delivery of the device. The integrated guide structure generally comprises one or more radiopaque markers to facilitate delivery under x-ray guidance. The guide structure can then be placed within the vasculature using appropriate hemostatic procedures and ports, and the distal tip can be navigated through the vasculature include tortuous paths, such as the cerebral vasculature. Due to a tortuous path, it may not be possible to direct the distal tip as far along the vasculature as desired due to friction within the vessel and bending of the device that deflects forces along the length of the structure. To avoid injury to a blood vessel, the forces applied to advance the guide structure should not be excessive. Once an integrated guide structure is advanced as far as practical, the corewire can be advanced an additional amount through the relative motion of the corewire relative to the overtube without significantly moving the overtube. The overtube supports the corewire along its length and a low friction coating between the corewire and overtube can reduce any friction between the corewire and overtube, so that the advancement of the corewire an additional distance can generally be performed without exerting large forces. In this way, the overall reach of the integrated guide structure can be extended a useful amount, such as at least about 1 centimeters up to about 10 centimeters, without injury to any blood vessels.

As explained in detail below, a suitable torque coupler can comprise a section of a corewire with an altered cross sectional shape and a corresponding section of the overtube that interfaces with the corewire section. In some embodiments, the torque coupler can also limit the longitudinal motion of the corewire relative to the overtube. The integrated guide structure can comprise a plurality of torque couplers to provide for additional angular stability due to fade of torque forces applied at or near one end of the integrated guide structure relative to the opposite end. A torque coupler may be between about 2 centimeters and about 15 centimeters in overall length. A person of ordinary skill in the art will recognize that additional ranges are contemplated and are within the present disclosure.

The corewire is configured to extend from both ends of the overtube, although in principle for some embodiments the corewire does not need to extend from the distal end of the overtube in a delivery configuration. In some embodiments, the corewire extends at least about 2 centimeters when the overtube is drawn in a proximal direction relative to the corewire. At the proximal end, the corewire and overtube can be translated relative to each other to change the extent of the corewire extending from the distal end of the overtube. In some embodiments, the distal end of the corewire has a coil, and for these embodiments, the distal end of the corewire with the coil always extends from the overtube. Also, generally, the device comprises radiopaque elements, such as marker bands, at and/or near the distal end of the components to help guide the placement of the guidewire in the vessel. Similarly, the distal end of the overtube can be cut and/or tapered with an optional coil or the like to increase the flexibility of the distal end of the overtube.

The various components of the integrated guide structures are appropriately designed to provide a first configuration with the distal tip of the corewire at a first position and a second configuration with the distal tip of the corewire extending a greater amount from the overtube at the distal end of the overtube. A backend tool can be attached at the proximal ends of the corewire and overtube to facilitate sliding of the corewire relative to the overtube and to reduce bending of the elements during this process. Several potential tool designs are described herein based on sliding designs or with a dial.

In a third set of embodiments, the distal end of a guidewire is configured with a flexible polymer extension with an asymmetric cross sectional shape, such as flattened in one plane. In some embodiments, the guidewire can have a corresponding asymmetric radiopaque marker so that the orientation of the tip can be evaluated. The flexible polymer extension can be oriented within the vessel to provide for the flow in the vessel to assist with guiding the tip. In some embodiments, the flexible tip has a greater diameter in one plane than the proximal wire component of the guidewire to provide for increased force due to the flow. The flexible tip can be rotated to increase or reduce the influence of the flow based on the asymmetry of the tip cross section. For example, if the flow is tending to direct a right or left turn, the plane of the flattened tip section can be oriented perpendicular to the turn so that the flow can bend the tip or parallel to the turn to resist bending in the direction of the flow change. Similarly, at a branch point in the flow, the flexible tip can be oriented and position to facilitate guiding the guidewire tip into one branch or the other branch. Conventional guidewires are delivered with a bent tip to provide for steering of the tip through the vasculature, and the flexible flattened tip provides for variable bending driven by the flow as an alternative approach to directing the guidewire.

The various embodiments of the guidewires described herein are designed to facilitate the performance of procedures in blood vessels or other bodily vessels having a tortuous path, i.e., a path with relatively sharp turns and the like. In particular, arteries in a human brain downstream from the carotid arteries, which can be referred to as neuro arteries, are known to have circuitous paths. Arteries in the brain are susceptible to serious acute events, such as embolic stroke events, and reaching the point of the event can be significant to provide for treatment. The guidewires described herein facilitate delivery of a treatment device or additional structures to further facilitate delivery of a treatment device.

With respect to the delivery of therapeutic devices over the guidewire, such devices can be directly tracked over the positioned guidewire. For example, an aspiration catheter can be tracked over a guidewire within a neuro artery. An aspiration catheter specifically designed for use in blood vessels in the brain are described in published U.S. patent application 2011/0230859 to Galdonik et al., entitled "Aspiration Catheters for Thrombus Removal," incorporated herein by reference. Similarly, angioplasty balloons or the like can be delivered over the guidewire. In additional or alternative embodiments, a further delivery tool, such as a microcatheter can be delivered over the guidewire, and then the guidewire removed prior to the delivery of a therapeutic device. For example, a fiber based clot engaging tool can be delivered through a microcatheter following placement of the microcatheter and removal of the guidewire. A fiber based clot engaging tool is described in U.S. Pat. No. 8,814,892 to Galdonik et al., entitled "Embolectomy Devices and Methods for Treatment of Acute Ischemic Stroke Condition," incorporated herein by reference.

The three sets of embodiments herein describe alternative approaches to achieve improved guidewire delivery especially into neuro arteries. The hyperbolic tapered catheters provide good distal flexibility with desirable control of the distal tip from manipulations at the proximal end. The integrated guide structure provides for additional extension of the distal end beyond what can be achieved through the guidance and force transmission along the length of the guidewire. The guidewires with the flexible polymer tips provide for steering in difficult vessel configurations using the flow itself to facilitate directing of the guidewire tip, and the great flexibility of the polymer reduces any potential injury to the vessel from the guidewire. The various embodiments may have particular advantages depending on the vessel architecture to be navigated. A person of ordinary skill in the art can select a desired device accordingly.

Guidewires with Hyperbolic Tapers

The guidewires in these embodiments generally comprise a solid metal wire extending a majority or all of the length of the guidewire, with a hyperbolic tangent shaped taper at or near the distal end, an optional coil at or near the distal end extending over at least a portion of the tapered wire, various securing elements and optionally one or more additional radiopaque elements. The length of the taper section can be selected based on the desired flexible extent of the guidewire, and coils can be designed accordingly. Generally, coils can be secured to the wire core at an end tab or weld and generally at another point such as at a hub or torque stabilizer, a proximal weld, combinations thereof or the like. In some embodiments, a coil can be attached slightly stretched to influence the mechanical properties of the distal tip.

The overall length of the guidewire can be selected for particular applications and generally for many medical applications range from about 90 centimeters to about 300 centimeters, in further embodiments from about 110 centimeters to about 280 centimeters, and in other embodiments from about 125 to about 250 centimeters. The distal tapered portion of the guidewire can involve from about 10 cm to about 60 cm, in further embodiments from about 15 cm to about 55 cm and in additional embodiments from about 20 cm to about 50 cm at the distal end of the guidewire. The hyperbolic taper, described further below, can extend to the distal end other than a distal feature such as a weld, tab or the like, or the hyperbolic taper can terminate before the distal end of the wire with an alternative shape wire extending to the distal end, such as an approximately constant diameter section. The hyperbolic taper can be formed using precision grinding, such as with a manual centerless grinder, chemical etching, laser ablation, extrusion, molding or the like. The diameter along a proximal shaft, generally with an approximately constant diameter, can be selected to be suitable for placement in desired vessels and for the delivery of selected devices over the guidewire. Generally, the diameter can be from about 0.0075 inches (in) about 0.03 in, in further embodiments from about 0.009 in to about 0.025 in, and in additional embodiments from about 0.01 in to about 0.02 in. Tolerances for commercial guidewire diameters can be plus/minus about 0.004 in, about 0.003 in or about 0.002 in. In one specific embodiment for neuro applications, the proximal portion of the guidewire can have a diameter of 0.0135 in ±0.002 in prior to applying a polymer coating and 0.0143 in after applying a polymer coating. A person of ordinary skill will recognize that additional ranges of dimensions within the explicit ranges above are contemplated and are within the present disclosure.

Referring to FIG. 1, guidewire 48 has distal end 50, proximal shaft 52, tapered segment 54 and distal portion 56. Tapered segment 54 has a taper shaped approximately according to a hyperbolic tangent that extends from the distal end of proximal shaft 52 to distal portion 56, with the diameter of the guidewire decreasing along the length of the tapered segment. The diameter of tapered segment 54 is wider at the point of contact with proximal shaft 52 than an its point of contact with distal portion 56. Distal segment 56 maintains approximate cylindrical symmetry around the central axis of the wire. Distal portion 56 may or may not be present in a specific guidewire embodiment. Distal portion 56 can have an approximately constant diameter, a different taper from tapered segment 54, a gradual increase in diameter to distal end 50 or a more complex variation in diameter which may or may not be monotonic. Proximal shaft 52 may be coated with a material to decrease the friction with in the blood vessel, for example, a friction reducing polymer such as polytetrafluoroethylene (PTFE) or other low friction biocompatible polymers. Distal portion 56 may be coated with a hydrophilic coating, such as a polyester, e.g., PET, polyether-polyurethanes, polycarboxylate polyurethanes, combinations thereof or the like. Tapered segment 54 and distal portion 56 and generally support a coil, and two such embodiments are presented below. Whether or not a coil is present, the distal end of the distal portion or tapered segment if a distal portion is not present can comprise a ball weld or the like, as shown in FIGS. 3 and 4.

FIG. 2 is a plot of an example of a hyperbolic tangent grind profile for tapered segment 54 of guidewire 48. Along the length of the taper profile, distal segment 54 narrows from its proximal end to its distal end. Tapered segment 54 can be characterized by the length and the diameter at its distal end since its diameter at the proximal end can coincide with the diameter of proximal shaft 52. In some embodiments, the length of tapered segment 54 can be from about 5 cm to about 60 cm, in further embodiments between about 10 cm and about 55 cm, or in additional embodiments between about 20 cm and about 50 cm. People of ordinary skill in the art will immediately appreciate that all values and ranges within the expressly stated ranges are contemplated, and are within the present disclosure. Hyperbolic tapers generally follow a hyperbolic tangent function. To eliminate a taper discontinuity due to a sudden change in taper slope, for example from grinding, at start and finish of the taper, one can initiate a taper contour starting with a slope near zero transitioning in the distal direction with a continuous or near continuous increasing slope grind taper and then transitioning in a continuous or near continuous decreasing slope taper until a taper slope of near zero is reestablished.

The diameter of the guidewire generally narrows from the proximal end of tapered segment 54 to the distal end of tapered segment 54. The narrowest point of the guidewire may be at distal tip 50 or it may be proximal to the distal tip if distal portion 56 increases in diameter from the distal diameter of the tapered segment. Generally, the diameter of distal portion does not vary by more than a factor of 2 as a ratio of its widest diameter to its narrowest diameter. In the embodiment corresponding to FIG. 2, distal portion 56 has a constant diameter extending to the distal tip. Distal portion 56 can have a length from about 0.5 cm to about 10 cm, in further embodiments from about 0.75 cm to about 7.5 cm and in further embodiments from about 1 cm to about 5 cm. The narrowest point of the guidewire may be from about 0.00033 in (8 microns) to about 0.006 in (152 microns), in further embodiments from about 0.00066 in to about 0.005 in and in other embodiments from about 0.001 in to about 0.0045 in. As a percentage of the widest diameter of the guidewire, the narrowest diameter of the guidewire can be from about 2.5% to about 90%, in further embodiments from about 10% to about 70% and in other embodiments from about 15% to about 50%. People of ordinary skill in the art will immediately appreciate that all values and ranges within the expressly stated ranges are contemplated, and are within the present disclosure.

As noted above, a guidewire with a hyperbolic taper generally further comprises a coil over at least a portion of distal portion 56 and tapered segment 54, and two specific embodiments are shown in FIGS. 3 and 4. Referring to FIG. 3, guidewire 60 comprises proximal shaft 62, tapered segment 64, optional distal portion 66 and a stretched coil 68. Proximal shaft 62, tapered segment 64 and optional distal portion 66 correspond with proximal shaft 52, tapered segment 64 and distal portion 56 of FIG. 1 and can have dimensional parameters spanning the same ranges described for the elements in FIG. 1. Coil 68 is located over distal portion 66 and the distal end of tapered segment 64. Coil 68 is attached at the distal end to ball weld 70 and at the proximal end to tapered segment 64 at braze 72. The coil may or may not be stretched. People of ordinary skill in the art will immediately appreciate that all values and ranges within the expressly stated ranges are contemplated, and are within the present disclosure. Braze 72 couples coil 68 to tapered segment 64 and can facilitate transmittal of rotational movement from proximal shaft 62. Braze 72 can be formed using a weld, solder, adhesive, a crimped ring, or other suitable mechanical or physical attachment.

In further embodiments, the guidewire further comprises a torque stabilizer to couple a location along the length of the coil to the tapered segment as depicted in FIG. 4. Referring to FIG. 4, guidewire 80 comprises proximal shaft 82, tapered section 84, optional distal portion 86 and coil 88. Coil 88 is located over distal portion 86 and at least a portion of tapered segment 84. Torque stabilizer 90 is positioned in a spaced away configuration relative to the ends of the coil to form a shapeable tip 92 between torque stabilizer 90 and ball weld 94. Torque stabilizer 90 couples coil 88 with tapered segment 84 in order to transmit rotational movement from proximal shaft 82. Shapeable tip 92 may be premade with a bent configuration, or it may be made of a material that can be bent and retain the bent shape. In alternative embodiments, a plurality of torque stabilizers can be used, such as two, three or more torque stabilizers. The torque stabilizer may be any suitable structure for coupling the coil and the guidewire including adhesive bonding, welding, soldering, crimping of the coil onto a hub, a lock and key structure interfacing the coil and a hub, friction fit to a hub secured to the tapered segment, or a combination thereof. Furthermore, a proximal braze can secure the proximal end of the coil while one or more toque stabilizers secure an internal segment of the coil. The coil may or may not be stretched between ball weld 94 and torque stabilizer 90. Stretching the coil may reduce the stiffness of the coil, softening the tip.

A coil associated with the distal end of the guidewire can have a length from about 1 cm to about 45 cm, in further embodiments from about 1.5 cm to about 40 cm and in additional embodiments from about 2 cm to about 35 cm. Relative to the combined length of the distal portion and tapered segment, the coil can have a length from about 2.5% to about 95%, in additional embodiments from about 4% to about 92.5%, and in additional embodiments from about 5% to about 90%. People of ordinary skill in the art will immediately appreciate that all values and ranges within the expressly stated ranges are contemplated, and are within the present disclosure. The coil may be formed form any reasonable biocompatible metals, such as stainless steel, titanium, spring metals such as cobalt alloys, for example Elgiloy®, a cobalt-chromium-nickel alloy, MP35N, a nickel-cobalt-chromium-molybdenum alloy, or Nitinol®, a nickel-titanium alloy, or combinations thereof. It may be desirable to form a coil from a more radiopaque metal, such as platinum or a platinum alloy, such as 92% platinum and 8% tungsten or platinum-iridium. The coil may or may not be covered with a polymer cover, which can be applied as a coating or through the placement of a thermoplastic polymer jacket, such as PET, that is heated to bond the polymer to the coil. While the coil can be formed from a radiopaque material, additionally or alternatively ball welds 70, 94, braze 72, torque stabilizer 90 or similar structures or portions thereof within a particular embodiment of a guidewire individually can be formed from or with a radiopaque material, such as such as platinum-iridium, platinum-tungsten or the like, or through radio-pacifiers, such as barium sulfate, bismuth trioxide, bismuth subcarbonate, powdered tungsten, powdered tantalum or the like, added to a polymer. Additionally or alternatively, a radiopaque marker band, such as marker band 96 in FIG. 4, formed of a radiopaque material can be placed along a tapered segment or other reasonable position along the guidewire.

Integrated Guide Structures with Extendable Tips

In these embodiments, the guidewires comprise an integrated guide structure having a corewire within an overtube that have some range at least of relative translation. In some embodiments, the distal end of the corewire has a coil placed over the corewire to reduce undesirable kinking of the corewire and to provide a more consistent outer diameter over most of the length of the guidewire. One or more torque couplers can rotationally couple the overtube and corewire to facilitate steering of the guidewire through rotation at the proximal end. The distal end of the overtube can be made more flexible through cutting of the overtube, grinding of the distal end of the overtube, and/or through the inclusion of a coil or near the distal end of the overtube. Several potential designs of proximal tools are described to facilitate sliding of the corewire within the overtube.

Figure 5:
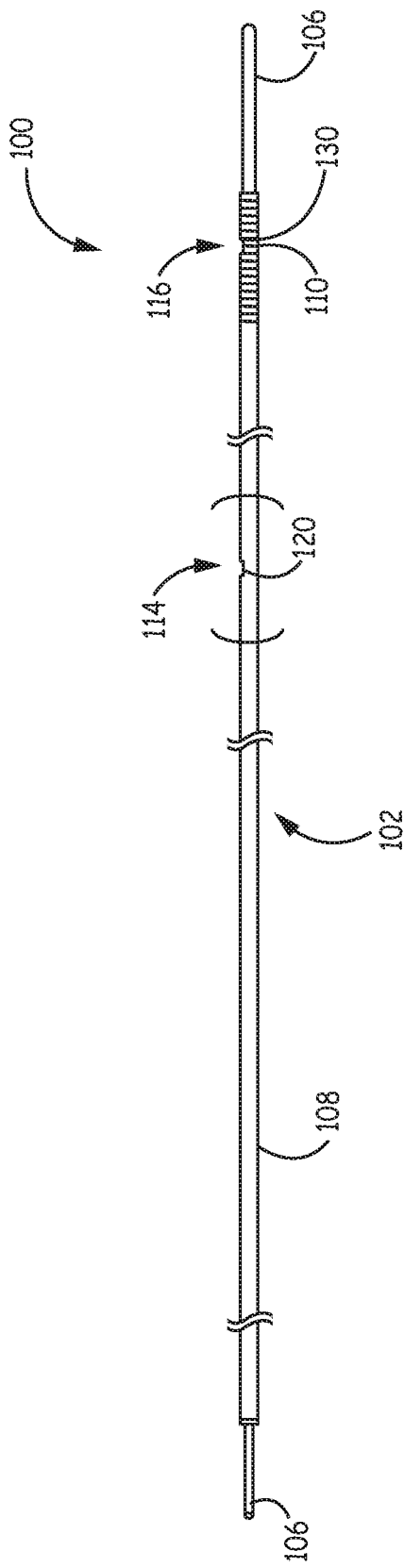
FIG. 5 is a side view of an extendable guidewire comprising a corewire and an overtube within an integrated guide structure.
Figure 6:
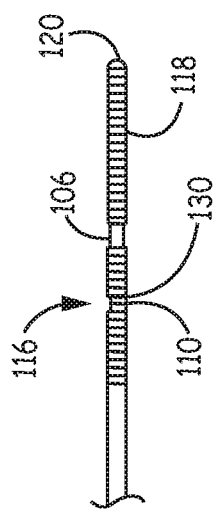
FIG. 6 is a fragmentary side view of a distal end of an integrated guide structure with a coil over the distal end of the corewire.

FIG. 5 shows an embodiment of a guidewire in the form of an integrated guide structure 100. In the depicted embodiment, integrated guide structure 100 comprises a corewire 106, overtube 108, a first resilient element 110, a first torque coupler 114, and a second torque coupler 116. Corewire 106 extends through a central lumen of overtube 108 with the distal end and the proximal end of the corewire extending from the overtube. First resilient element 110 covers a portion of corewire 106, and first resilient element 110 can extend from the distal end of overtube 108 or overlap with a portion of the distal end of overtube 108. In some embodiments, a second resilient element 118 is located at the distal tip of corewire 106 as shown in FIG. 6. The presence of a second resilient element 118 constrains the distal end of corewire 106 to extend from the end of overtube 108 including first resilient element 110 as an extension of the distal end of overtube 108. Second resilient element 118 is secured to corewire 106 at or near the distal end of the device, for example, with adhesive, by welding or mechanical crimping, with solder, combinations thereof or the like. In particular, a welded tip 120 can be placed at the distal tip of corewire 106. Torque couplers 114, 116 can have appropriate structure, described further below, to rotationally couple corewire 106 with overtube 108 and corewire 106 with first resilient element 110, respectively. In some embodiments, only one of torque coupler 114 or 116 are included, such as only torque coupler 114 with torque coupler 116 absent, and in additional embodiments a third, fourth or more torque couplers are include at appropriate positions along overtube 108 and/or first resilient member 110.

Figure 7:
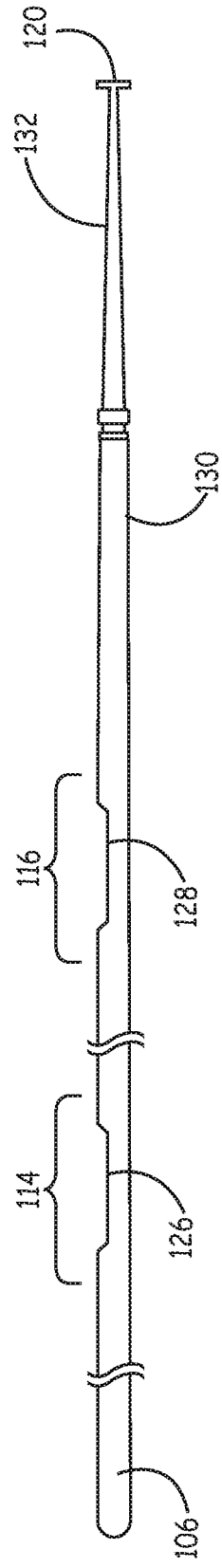
FIG. 7 is a side view of the core wire of the guidewire of FIG. 5 separate from the remaining components of the integrated guide structure.

Referring to FIG. 7, corewire 106 is shown separated from overtube 108 and second resilient element 118. Corewire 106 has a first flattened section 126 and a second flattened section 128 that form keyways for torque couples 114, 116, respectively. Distal segment 130 is tapered, and a distal tip 132 is tapered and optionally flattened along a portion over which second resilient element 118 is placed. Weld 120 is located at the distal tip of corewire 106. In some embodiments, corewire 106 can have one or more deliberate notches, such as in the proximal half of the corewire, to provide for a controlled slight amount of friction between the corewire and overtube.

The resilient elements provide segments of greater flexibility relative to the overtube flexibility. It can be desirable for the distal end of the guidewire device to have greater flexibility for navigating bends and branches along the vessels. In general, a resilient member has an overall tubular shape with a central lumen for the passage of the corewire. In general, the increased flexibility of the resilient member is achieved through a structure that lacks a solid uniform wall. Also, decreasing the wall thickness at or near the distal end provides increased flexibility. For example, the wall thickness can be machined down, and a polymer jacket, such as a heat shrink polymer, can be placed over the thinned wall to maintain an approximately uniform outer diameter as well as smoothing out potential edges. For example, resilient elements can comprise a coil and/or the tube with a coil pattern or slots cut into and/or through the tube. Also, it is desired that the resilient elements have a construction such that torsional force can be transferred without significant loss along the length of the section. The transfer of torsional force enhances steerability of the tip. As a result, if a coil or other appropriate resilient structure is used, the resilient element can be rotationally locked to a portion of the corewire such as by creating circumferential mechanical interference between the two members.

As shown in FIG. 6, second resilient element 118 is a coil that is secured proximal to weld 118. In alternative embodiments, the coil can be replaced with a portion of cut tubing or a combination of cut tubing and one or more coil(s). Similarly, first resilient element 110 can be a coil secured to overtube 108. Resilient element 110 can be attached directly, or indirectly with a spacer or the like, to the distal end of overtube 108, or resilient element 110 can overlap with a portion, such as a tapered portion, of overtube 108. As with second resilient element 118, first resilient element 110 can comprise cut tubing or a combination of cut tubing and one or more coils, as an alternative to a coil. In general, first resilient element 110 and second resilient element 118 can have any reasonable longitudinal lengths and outer diameters roughly equivalent to the outer diameter of overtube 108 or a slightly reduced outer diameter. In some embodiments, first resilient element 110 can have a length of no more than about 40 centimeters and in further embodiments from about 1 centimeter to about 30 centimeters. In some embodiments, second resilient 118 can have a length of no more than about 20 centimeters and in further embodiments from about 0.5 centimeter to about 15 centimeters. A person of ordinary skill in the art will recognize that additional ranges of resilient element dimensions within the explicit ranges above are contemplated and are within the present disclosure.

Figure 8A:
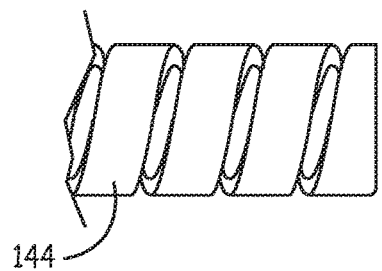
FIG. 8A is an expanded fragmentary view of the spiral cut portion of a resilient element.
Figure 8B:
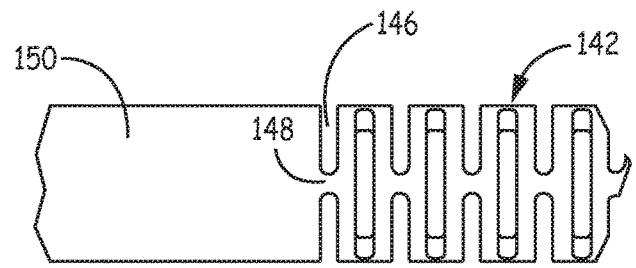
FIG. 8B is an expanded fragmentary view of a resilient element with cut slots adjacent an uncut section of the overtube.

The inner diameter of the resilient members should be at least large enough to accept the corewire. The outer diameter generally is similar to the outer diameter of the overtube. A person of ordinary skill in the art can select the dimensions and elasticity of the coil to yield desired degrees of flexibility. Referring to FIG. 8A, a first resilient member 144 has a spiral cut. The spiral cut provides for a slight expansion of the inner diameter as well as additional flexibility. Referring to FIG. 8B, first resilient member 142 comprises pairs of opposing slots 146 are cut through the tube with rails 148 connecting the opposing slots. Pairs of adjacent opposing slots are rotated about 90 degrees relative to each other. The dimensions and spacing of the slots can be selected to achieve desired resiliency. As shown in FIG. 8B, resilient member 142 is cut into overtube 150 such that they are integral members of the structure. Suitable cutting techniques for cutting an overtube include, for example, mechanical cutting, electrostatic discharge machining (EDM), cutting with high pressure fluids, chemical etching and laser cutting. Laser cutting can be particularly efficient for the formation of a significant number of precision cuts using automated control, especially cuts that penetrate through the catheter/tube to the inner lumen. Etching may be particularly effective to form slots that do not penetrate through the material of the overtube.

Further details and options on resilient members are disclosed in U.S. Pat. No. 8,092,483 to Galdonik et al. (the '483 patent), entitled "Steerable Device Having A Corewire Within A Tube and Combination With A Functional Medical Component," which is incorporated herein by reference.

The length of overtube 104, e.g., a hypotube or a polytube, can generally be selected for the particular application. For example, for intervention in various blood vessels, the overtube generally would have a length from about 100 cm to about 300 cm. Corewire 106 is longer than overtube 104 with the corewire extending from the proximal end of the overtube in all functional configurations to provide control of the relative position of the corewire, and corewire 106 extends from the distal end of the overtube as extended by first resilient element 110 at least in configurations in which the corewire is moved in a relative distal direction relative to the overtube, as discussed further below. The cross section of the overtube can be characterized by an inner diameter and an outer diameter. The inner diameter general ranges from about 0.001 inches to about 0.03 inches, in further embodiment from about 0.003 inches to about 0.02 inches and in additional embodiments from about 0.005 inches to about 0.01 inches. The outer diameter generally ranges from about 0.005 inches to about 0.04 inches, in further embodiments from about 0.007 inches to about 0.03 inches, in additional embodiments from about 0.008 inches to about 0.02 inches and in other embodiments from about 0.009 inches to about 0.015 inches, with standard guidewire outer diameters being about 0.010 inches to 0.014 inches. The proximal segment of the corewire generally has a diameter just slightly less than the inner diameter of the tube by about 0.001 inches to about 0.003 inches. A person of ordinary skill in the art will recognize that additional ranges within the explicit ranges for the diameters are contemplated and are within the present disclosure.

In general, corewire 102, overtube 104 and resilient elements 106, 108 can be formed from one or more of various materials, such as polymers, metals and combinations thereof. The overtube and corewire may or may not be formed from the same material. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, Nitinol®, a nickel-titanium alloy or a combination thereof.

Suitable polymers include, for example, synthetic polymers as well as purified biological polymers and combinations thereof. Suitable synthetic polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

In other embodiments, the surface of the corewire, the inner surface of the overtube, the outer surface of the overtube, portions thereof or combinations thereof is coated with a friction reducing agent. Suitable friction reducing agents include, for example, suitable polymers, such as polytetrafluorethylene, i.e., Teflon® or a polymer coating such as parylene. The coating of the corewire or a portion thereof can facilitate relative longitudinal motion of the corewire relative to the overtube.

Torque couplers are generally formed by components of the integrated guiding device engaging with each other. In some embodiments, the components engage by the mechanism of a protrusion fitting within a depression. FIG. 5 shows an assembled guidewire 100 comprising an integrated guiding device with portions of torque couplers 114, 116 shown as indentations or notches 120, 130 in overtube 104 and first resilient element 116, respectively. These indentations 120, 130 form keys or key-like structures which engage with the flattened keyway portions 126, 128 formed in the corewire 102 as shown in FIG. 7.

The torque couplers provide for a range of lateral motion of corewire 102 relative to the overtube 104. Specifically, the lateral length of the flattened keyway and the size of the indentation provide constraints on the relative lateral movement. In some embodiments, the corewire can move no more than about 10 centimeters (cm), in further embodiments from about 0.25 cm to about 5 cm and in additional embodiments from about 0.5 cm to about 4 cm. If second resilient element 118 is present, corewire 106 extends beyond the distal end of overtube 104 as extended with first resilient element 110 in all configurations, but in embodiments without second resilient element 118, the corewire may or may not extend beyond the distal end of overtube 104 with first resilient element 110. In a configuration with the corewire moved in a relative proximal direction relative to overtube 104, second resilient element 118, if present, can approximately abut first resilient element 110 or if second resilient element 118 is not present, corewire 106 can extend from overtube 104 with first resilient member 110 by a reasonable amount, such as the range of lengths of second resilient member noted above. A person of ordinary skill in the art will recognize that additional ranges of relative sliding of the corewire and overtube within the explicit ranges above are contemplated and are within the present disclosure.

Figure 9A:
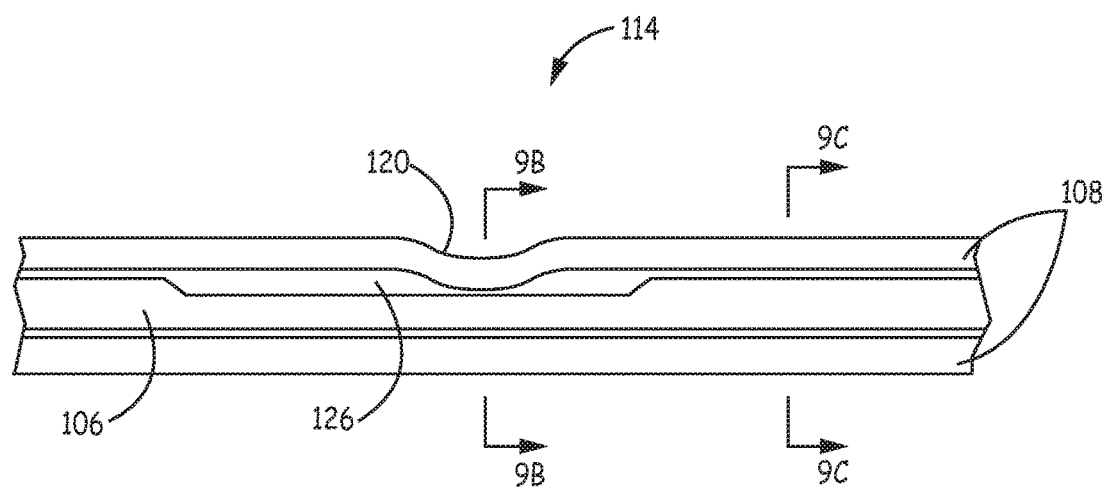
FIG. 9A is an expanded fragmentary side view of the torque coupler of FIG. 5 that interfaces the overtube with the corewire.
Figure 9B:
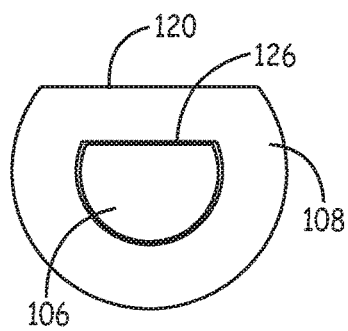
FIG. 9B is a sectional view of the torque coupler taken at line 9B-9B in FIG. 9A.
Figure 9C:
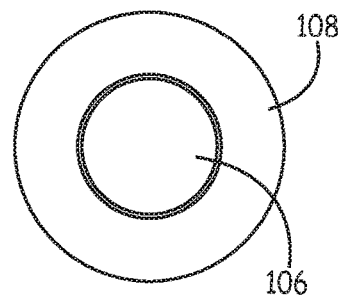
FIG. 9C is a sectional view of the corewire and the overtube taken outside the torque coupler at line 9C-9C of FIG. 9A.

Referring to FIG. 9A, first torque coupler 114 rotationally couples corewire 106 with overtube 108. The walls of overtube 108 comprise an indentation 120 on the outer surface defining a downward protrusion along the inner diameter that fits into flattened keyway portion 126 on the outer surface of corewire 106. The length of keyway 126 specifies limits on the relative longitudinal motion of the corewire relative to the overtube. FIG. 9B shows a sectional view of the integrated guiding device taken along torque coupler 114, which is shown as flattened areas interfacing each other due to structure from indentation 120 and flattened portion 126. As a comparison, FIG. 9C shows a sectional view of the integrated guiding device taken along an area outside torque coupler 114. One of ordinary skill in the art would recognize that overtube 108 and corewire 106 can have different shapes for the cross sectional interface regardless of whether the sectional view is taken at the torque coupler or at an area outside the torque coupler.

Figure 10A:
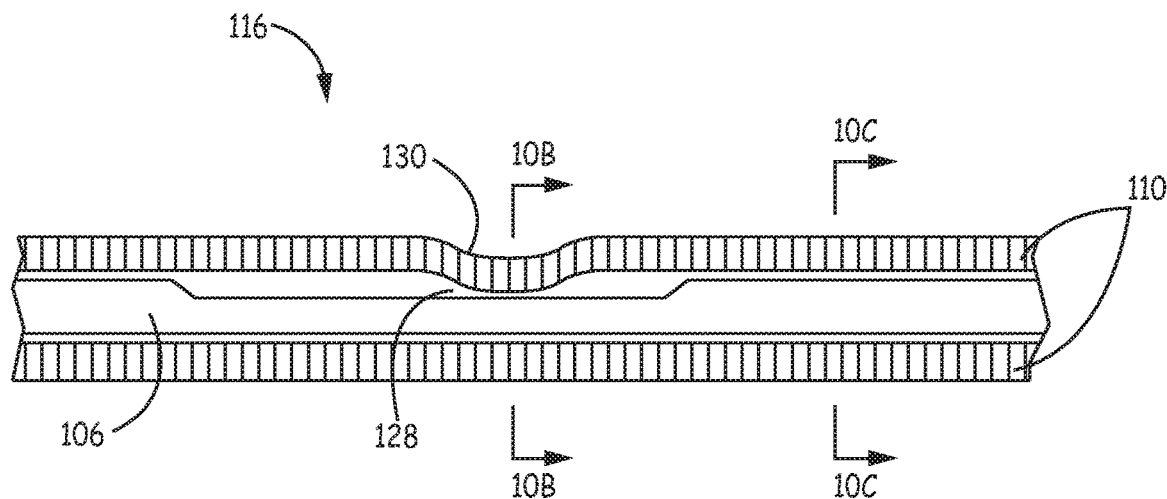
FIG. 10A is an expanded fragmentary side view of the torque coupler of FIG. 5 that interfaces the resilient element with the corewire.
Figure 10B:
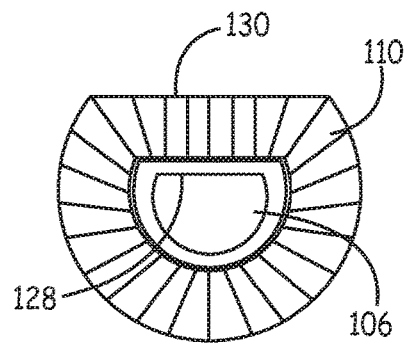
FIG. 10B is a sectional view of the torque coupler taken at line 10B-10B in FIG. 10A.
Figure 10C:
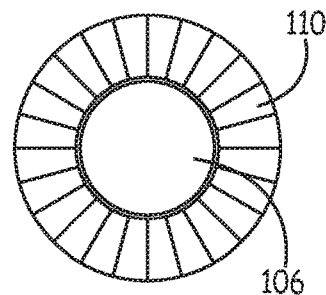
FIG. 10C is a sectional view of the corewire and the resilient element taken outside the torque coupler along line 10C-10C of FIG. 10A.

Referring to FIGS. 10A-10C, expanded sectional views are displayed for second torque coupler 116. Referring to FIG. 10A, torque coupler 116 rotationally couples the corewire 106 with resilient element 110. If the resilient element 110 comprises a coil, a section of coil has an indentation 130 defining a downward protrusion along the inner diameter of the coil that fits into flattened keyway portion 128 of corewire 106. The coil covers a section of corewire 106, extending from roughly the distal end of the overtube 108.

Regardless of whether the resilient element comprises a coil or a cut portion of the overtube, the resilient element is shaped to provide a protrusion that engages with a flattened segment formed in the corewire. The length of flattened keyway portion and the size of the key further constrains the range of lateral motion of the corewire relative to the overtube available without damaging the device. FIG. 10B shows a fragmentary sectional view of the integrated guiding device taken through torque coupler 116. Torque coupler 116 has flattened areas engaging each other as a result of the structure of protrusion 130 and flattened portion 128. As a comparison, FIG. 10C shows a sectional view of the integrated guiding device taken along an area outside torque coupler 116 along resilient member 110. In contrast to the semi-circular cross section of the corewire in FIG. 10B, the sectional view taken outside torque coupler 116 has a circular cross-section. One of ordinary skill in the art would recognize that coil 106 and corewire 102 can have different cross sectional shapes as long as the elements are mated to engage properly while providing for some relative lateral movement. There are significant advantages to having a torque coupler interfaced with the resilient member. While the resiliency of the resilient member affords the flexibility to provide for the steering of the guidewire, it also causes the resilient member to distort in shape, which decreases the torque transfer from the proximal end to the distal end of the guidewire. A torque coupler interfacing the resilient member with the corewire would rotationally couple the resilient member with the corewire to decrease distortion of the resilient member around the corewire and increase the transfer of torque from the proximal end to the distal end of the corewire. Surprisingly, the resiliency of the resilient member generally does not detract from the ability to function as a torque coupler.

A variety of alternative structures are possible for torque couplers in addition to the lock and key embodiments discussed specifically above. Some alternative embodiments are described in more detail in the '483 patent cited above and incorporated herein by reference.

Figure 11A:
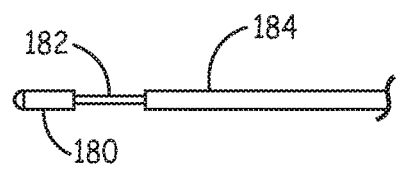
FIG. 11A is a fragmentary side view of an integrated guide structure with a handle secured to the proximal end of the corewire.
Figure 11B:
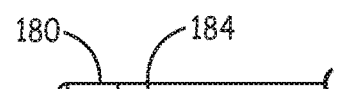
FIG. 11B is a fragmentary side view of the device of FIG. 11A in an extended configuration with the corewire translated in a distal direction relative to the overtube.

It is generally desirable to change the relative longitudinal position of the corewire and overtube at appropriate points in a procedure. To limit kinking of a very thin corewire as well as to facilitate the manipulation of the movement of the corewire relative to the overtube, various tools can be used. Referring to an embodiment in FIGS. 11A and 11B, a handle 180 is secured to the proximal end of corewire 182. Handle 180 can be used to grip corewire 182 to effectuate relative motion of corewire 182 and overtube 184. As shown in FIG. 11A, corewire 182 is in a relative proximal orientation relative to overtube 184, which can be used during delivery of the guideiwre. Once overtube 184 is in position, corewire 182 can be moved to the configuration shown in FIG. 11B with corewire moved in a relative distal direction so that the distal end of corewire 182 can advance further within the blood vessel.

An embodiment of an actuation tool providing for rotational motion of dial to change the relative position of corewire and overtube is depicted in FIGS. 12 and 13. Referring to FIG. 12, an actuation tool 200 comprises a support structure 202, a corewire connection 204 and an overtube connection 206 each connected to opposite ends of the support structure 202, a dial 208, and a button lock 210. Corewire connection 204 and overtube connection 206 interface with support structure 202 along a channel 220 that provides for passage of the corewire, as shown in FIG. 13. Corewire connection 204 and tube connection 206 are gripping devices that respectively grip the corewire and overtube when engaged to provide for their relative longitudinal movement through rotation of dial 208.

Referring to FIGS. 12-13, in this embodiment, corewire connection 204 and overtube connection 206 are collets that comprise, respectively, threaded receiving sleeves 222, 224 and mated threaded caps 226, 228. Receiving sleeves have a taper and one or more slits such that channels through the receiving sleeves shrink in diameter when the mated cap is tightened such that the respective collets grip the overtube or corewire upon tightening. As shown in FIG. 14, sleeve 222 is integral with arm 238 that is securely attached to housing 202. Cap 226 can comprise a window 240, as shown in FIG. 13, for observing the corewire, such that it can be quickly determined if the corewire is properly loaded in the actuation tool. Referring to FIG. 13, corewire tubular channel 241 is connected to sleeve 222 to form a continuous corewire path into cap 226. Sleeve 224 is connected to sliding arm 242. Sliding arm 242 has an overtube channel 244, an overtube stop 246 that provided a limit on the insertion of the overtube with a corewire tubular channel 248 connected to sliding arm 242 extending beyond the overtube stop. Corewire tubular channel 248 has an inner diameter slightly larger than the outer diameter of corewire tubular channel 241 so that corewire tubular channel 248 slides over corewire tubular channel 241 when sliding arm 242 moves such that the corewire is supported essentially along its entire length within actuation tool 200.

While the embodiment shown in FIGS. 12-13 is based on collets, corewire connection 204 and overtube connection 206 can be based on other designs. For example, connections 204, 206 can comprise clamps that snap between locked and unlocked configurations, in contrast with the collets that screw into position. In some embodiments, a lever arm can be used to transition the connections between locked and unlocked positions. Various clamps designs in the art can be adapted as substitutes for the collets based on the disclosure herein.

Referring to a cut away exposed view in FIG. 13, the components internal to the support structure 202 comprises a control element that moves the corewire connection and the tube connection away from and toward each other to move the corewire and tube away from and toward each other, respectively. Support structure 202 comprises housing and cover that attached to housing to cover the moving parts within housing. The control element can include a transmission comprising gear 254 that interfaces with sliding arm 242 such that rotation of gear 254 is converted to translation motion of sliding arm 242 such that the position of corewire connection 204 and overtube connection 206 can be adjusted. In particular, gear 254 and sliding arm 242 comprise teeth that cooperate with each other. Gear 254 is operably connected to a knob 256 that connects with dial 208. When dial 208 is rotated, gear 254 rotates with the dial 208 and the gear's teeth cooperate and move with the teeth of sliding arm 242 to convert the rotational movement of the dial 208 and gear 254 to translational movement of sliding arm 242 to move corewire connection 204 relative to tube connection 206. Other transmission designs for converting rotational motion of the rotatable element to a translational motion of the corewire connection or the overtube connection can replace the design shown in FIG. 13 if desired.

Cover comprises a first hole for the passage of a portion of knob 256 to provide for connection to dial 208 and a second hole for the passage of depressible button 210. Cover can further comprise markings to provide instructions. Dial 208 comprises a notch that engages with safety button 210 at a particular rotation of dial 208 to prevent rotation of the dial 208 unless the safety button 210 is depressed. Safety button 210 can be constructed with a spring, such as a conventional spring structure or the like, or with other elastic material or appropriate construction. In some embodiments, notch is positioned to engage safety button 210 at a dial position corresponding with a particular relative position of the corewire and overtube. Actuation tool 200 can be supplied with a removable shipping lock that interfaces with dial 208 and cover to supply the dial at a particular orientation. Shipping lock can be kept in position until the guidewire is placed within the patient and the operator is ready to deploy the treatment element. Shipping lock can be removed to deploy the treatment element within the patient. In alternative or additional embodiments, a second depressible button or the like can be used to hold dial 208 at a delivery position to resist premature deployment of the device. Furthermore, other appropriate locking features, such a frictional catch or the like, can replace the button lock to provide fixed positions of the dial at the deployed and/or delivery positions of the dial.

Referring to FIG. 13, a cut away exposed view of actuation tool 200 reveals the components internal to sliding arm 242 and arm 238. Arm 238 has a projecting sleeve 274 that extends within sliding arm 242 to facilitate the sliding motion of sliding arm 242 while keeping the channel aligned for the corewire. The clearance between the adjustable corewire channel 248 and the corewire can be less than or equal to about 0.003 inch. Adjustable corewire channel 248 can provide appropriate support for the entire length of the corewire exposed from the overtube through the locked position within the corewire connection 204. In some embodiments, adjustable corewire channel 248 extends to leave less than about 0.001 inch of the corewire unsupported between the position at which the corewire exits the overtube and the locked position in corewire connection 204.

In operation, actuation tool 200 is constructed to extend the length of the guidewire by taking an advantage of the configuration of the integrated guiding structure with the proximal end of the corewire extending from the proximal end of the tube. The proximal end of the corewire is inserted through overtube connection 206 and adjustable corewire channel 248 into the corewire connection 204. The overtube contacts stop 246 to indicate full insertion of the overtube into overtube connection 206. The user can observe the corewire within observation window 240 to confirm that the corewire is properly positioned within the corewire connection 204. After the corewire is properly positioned corewire connection can be locked onto the corewire, and overtube connection can be similarly locked onto the overtube either before or after locking the corewire connection. Dial 208 can be rotated to extend the distal end of corewire out further from the distal end of the overtube. When dial 208 is rotated clockwise, gear 254 also rotates clockwise and causes translational movement of sliding arm 242 away from corewire connection 204, which increases the length of adjustable channel 248. When dial 208 is rotated counterclockwise upon depressing button 210, gear 254 also rotates counterclockwise and causes translational movement of sliding arm 242 toward corewire connection 204, which decreases the length of adjustable channel. If desired, the actuation tool can be temporarily removed for the loading of other instruments over the integrated guide structure.

In some embodiments it is desirable for the corewire to move relative to a fixed overtube and actuation tool housing. In these embodiments the actuation tool can be modified so that the overtube and corresponding overtube connection is fixed relative to the housing while the corewire and corresponding corewire connection translates with the sliding arm. Rotation of the dial then moves the housing along the overtube, moving the corewire relative to the fixed overtube.

Another alternative embodiment for the actuation tool is shown in FIGS. 14 and 15. Referring to FIGS. 14 and 15, actuation tool 300 comprises a housing 302, a loading funnel 304, a viewing window 306, a lift cover 308, and an actuation dial 310. Referring to FIGS. 14 and 15, lift cover 308 has a closed position in which cover 308 is enclosed. When lift cover 308 is closed, then gripping elements are open so that the integrated guide structure can be inserted through loading funnel 304 into housing 302. Referring to FIG. 15, cover 308 opens to an actuation position where the cover snaps into position to expose dial 310. Placement of cover 308 in the actuation position locks the overtube and corewire in position within housing 302. Then, with access available, dial 310 can be rotated between an initial position 312 and an extended guidewire position 314. Thus, to load a tool such as an aspiration catheter or a stent delivery catheter over the integrated guide structure, cover 308 can be placed in the closed position to release the integrated guide structure, which is then disconnected from the actuation tool for loading of the catheter and then replaced into the actuation tool. While the integrated guide structure is disconnected from the actuation tool, the dial cannot be accidentally rotated since it is covered.

Figure 16:
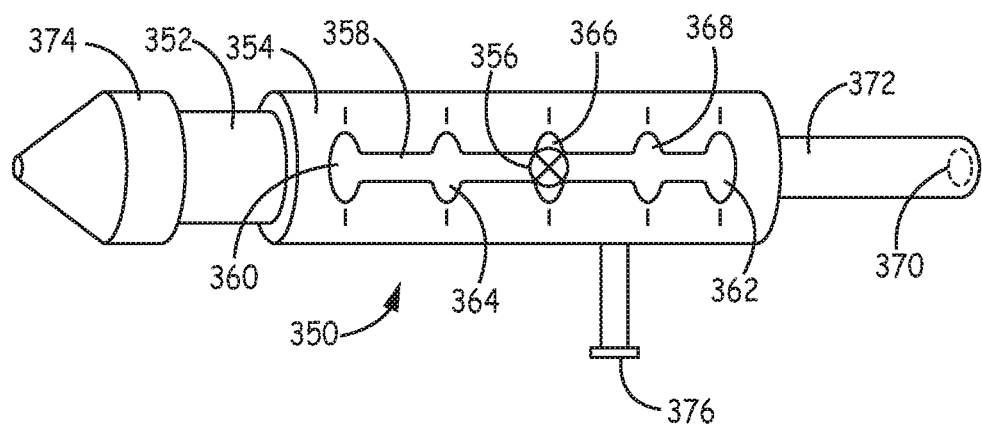
FIG. 16 is a fragmentary side perspective view of a further alternative embodiment of a pull element with intermediate locking positions between the limits of the range of motion.

A less complex tool is depicted in FIG. 16. While continuously adjustable positioning can be advantageous, other types of intermediate positioning may also have desirable features in some embodiments. In general, some embodiments have one intermediate stop point as well as stop points at the two ends of the range of motion while in other embodiments there are more than one intermediate stop point with the number of stop points selected as desired. Referring to FIG. 16, an embodiment of an actuation tool is shown with a ratchet style pull element 350. Pull element 350 comprises slide 352 and body 354. Button 356 is attached to slide 352. Body 354 has a slot 358 that constrains the position of the button 356. In this embodiment, slot 358 has two end stop points 360, 362 and three intermediate stop points 364, 366, 368. Markings can label the particular stop points. The operator can select the particular stop point to position corewire 370 at one of the end points of its range of motion or at an intermediate stop point relative to overtube 372. Slide 352 releasably secures to corewire 370, for example, with a tightening collet 374 or other suitable releasable attachment device. Similarly, body 354 can releasably secure to overtube 372, for example, through the tightening of a screw 376 or other suitable releasable fastener. Friction based ratchet structures can be similarly used. In other embodiments, one interment stop point, two intermediate stop points, four intermediate stop points, five intermediate stop points, ten intermediate stop points, twenty intermediate stop points, or any number in between can be used as an alternative to the three intermediate stop points shown in FIG. 16 based on the disclosure herein.

Guidewires with Flow Steerable Tips

In contrast with traditional guidewires, guidewires with flexible polymer tips have been designed to introduce a momentary adjustment or bend of tip orientation by the surrounding flow rather than through permanent deformation of the tip by the operator before insertion into the body. With this new flow directed bend, the guidewire can be used more effectively in other areas of the vasculature where a permanent deformation or bend of the tip section would limit easy passage. The flexible polymer tip has a flattened or sail like profile designed to selectively engage or not engage with the local fluid flow to allow the flow forces to bend or bias the tip towards the selected flow pathway or to be indifferent to it. To control tip bending, the flattened profile section along the tip can be rotated to enhance the interaction with the nearby flow to enhance the flow's ability to bend the tip or the tip can be rotated to reduce or effectively eliminate the surrounding flow's ability to bend the tip. In particular, at a branch in the vasculature, the flow splits. The change in flow provides corresponding changes in hydrodynamic forces in the vessel at different locations across the vessel. To divert the flattened tip into one branch vessel's flow or the other, the tip position can be adjusted axial and rotationally to catch the targeted vessel's flow or not. Thereby, at a branch the flow itself can direct the tip of a normally straight guidewire tip into one vessel or the other. Once the guidewire tip section is within the selected side branch, the tip would reestablish a generally straight orientation, best suited for further safe passage into the vessel.

Referring to FIGS. 17 and 18, a first embodiment of a guidewire 400 having a flexible polymer tip is depicted in a first orientation (FIG. 17) with a thin edge of the tip that can cut through the flow and in a second orientation (FIG. 18) with a flow engaging surface along the plane of the figure. Guidewire 400 comprises an elongated wire 402, polymer tip 404, an asymmetric radiopaque band 406, and asymmetric radiopaque tip element 408. Elongated wire 402 generally can comprise shaft 410 and engagement segment 412. Shaft 410 can comprise a solid metal wire, a tubular element, a coil structure, or other reasonable construction. Shaft 410 can be formed from biocompatible metals, such as discussed above for the other guidewire embodiments. While in principle polymer tip 404 can abut elongated wire 402, generally it is desirable to have a region of overlap to facilitate formation of a strong bond between the elements. Thus, engagement segment 412 forms a portion of elongated wire 402 that overlaps with polymer tip 404.

Engagement segment 412 can be designed with various shapes, and this element can have a taper and/or one or more step downs in diameter to reduce diameter for overlap with polymer tip 404 as well as approximately constant diameter segments or alternative shapes. One embodiment of engagement segment 412 is depicted in FIGS. 17 and 18. In this embodiment, engagement segment 412 has a taper portion 414 and extension 416, which has an approximately constant diameter but with flattened surfaces 418, 420. An alternative embodiment of an engagement segment is shown in FIG. 19, which can be substituted for engagement segment 412. Various other variations on engagement segments 412 can be used based on the teachings herein.

Polymer tip 404 generally comprises a transition portion 430 and a deflection portion 432. Transition portion 430 generally tapers in one dimension as shown in FIG. 17 while maintaining an approximately constant dimension or changing dimension a small amount, either smaller or larger, in the dimension rotated 90 degrees (FIG. 18). The amount of taper of the transition portion can be, for example, at least about 50% of the diameter of shaft 410, in further embodiments from about 55% to about 97.5% and in further embodiments from about 60% to about 95%. A person of ordinary skill in the art will recognize that additional ranges of taper within the explicit ranges above are contemplated and are within the present disclosure. With respect to deflection portion 432, this element can be relatively flat in the non-tapered plane or it can have other contours suitable to facilitate engaging the flow, such as a concave shape. Also, deflection portion 432 can comprise reinforcement elements, such as ribs or metal reinforcements to provide some physical resilience to the deflection portion. Suitable polymers for polymer tip 404 include, for example, nature rubber, polyisoprenes, polybutadiene, neoprene, butyl rubber, nitrile rubber, silicone, butyl rubber, ethylene propylene rubber, polyacrylic rubber, polyurethanes, mixtures thereof or the like. In some embodiments the polymer tip is flexible enough to bend, but not so flexible as to be collapsed by the flow. If metal reinforcement is desired for polymer tip 404, suitable biocompatible metals are described above, and metal reinforcements can be incorporated into the rubber tip with heating of the polymer, adhesives or other suitable approach.

Marker band 406 can be designed to facilitate visualization of the orientation of guidewire 400 within the patient's vessel. As shown in FIGS. 17 and 18, marker band 406 has radiopaque sections 440, 442 relative to less radiopaque segments along the remainder of the band. For example, a portion of the band can be formed from stainless steel while radiopaque sections 440, 442 can be formed from platinum alloy or other radiopaque material, as summarized above. In some embodiments marker band 406 is circumferentially asymmetric. While various designs can be used to provide an asymmetric visualization element, as shown in FIGS. 17 and 18 assuming that the x-rays are transmitted perpendicular to the plane of the figures, a larger radiopaque image is cast by marker band 406 in the orientation of FIG. 17 relative to the orientation of FIG. 18. In alternative embodiments, marker band 406 can be rotated 90 degrees to provide a larger radiopaque image in the orientation of FIG. 18. Marker band 406 can be placed at any reasonable location along the distal 25% of the guidewire length, so the position shown in FIG. 17 is just one optional location. As shown in the embodiment of FIG. 19, a marker band is located at the overlap of the elongated wire and the polymer tip, which can provide some reinforcement of the bonded elements, and a comparable location can be used for marker band 406. As shown in FIGS. 17 and 18 a single marker band is shown, but two, three or more marker bands, which individually may or may not be asymmetric, can be used if desired to facilitate visualization. Asymmetric radiopaque tip element 408 can be shaped to conform to the tip of deflection portion 432 to provide natural asymmetry, although it can deviate somewhat from the adjacent polymer without significantly altering the asymmetry. Tip element 408 can be formed from radiopaque metal, such as platinum alloy, loaded polymer with a radiopaque material, or the like. Similarly, the flattened shaped tip can be loaded with a radiopaque filler or the like, such as barium sulphate in order to visualize the bend caused by the flow.

An alternative embodiment of a guidewire with a flow orientable tip is shown in FIG. 19 in which the polymer tip has a deflection portion that can unfurl to have an edge to edge distance greater than the diameter of the proximal shaft. An orientation rotated 90 degrees relative to FIG. 19 is not shown, but is similar to the view of FIG. 17 with corresponding changes provided with respect to the comparison of FIGS. 18 and 19. Guidewire 450 comprises an elongated wire 452, polymer tip 454, an asymmetric radiopaque band 456, and asymmetric radiopaque tip element 458. Elongated wire 452 generally can comprise shaft 460 and engagement segment 462. Shaft 460 can comprise a solid metal wire, a tubular element, a coil structure, or other reasonable construction. Shaft 460 can be formed from biocompatible metals, such as discussed above. As discussed above for engagement section 412, engagement section 462 can have various reasonable configurations. As shown in FIG. 19, engagement section 462 has a taper and expansion that can provide for enhanced engagement between the engagement section 462 and polymer tip 454. Asymmetric radiopaque band 456 comprises radiopaque sections 470, 472 and is located along the interface region between engagement section 462 and polymer tip 454 to further secure the polymer tip. Radiopaque band 456 can be constructed similarly to marker band 406 described above. Also, asymmetric radiopaque tip element 458 is similar to asymmetric radiopaque tip element 408 and can be formed from equivalent materials.

Polymer tip 454 generally comprises a transition portion 480 and a deflection portion 482. Transition portion 480 generally tapers in one dimension such as shown in FIG. 17 for the embodiment in that figure, while maintaining an approximately constant dimension or changing dimension a small amount, either smaller or larger, in the dimension rotated 90 degrees (FIG. 19). The amount of taper of the transition portion can be within the same ranges discussed above for transition region 430. Deflection portion 482 has an extended diameter in the orientation of FIG. 19 relative to the diameter of shaft 460. Generally, deflection portion 482 can be flexible enough so that it can be collapsed to a lower profile configuration for delivery into the vessel through a microcatheter, guide catheter or a suitable fitting, such as a Luer lock or other hemostatic fitting, such as those known in the art. The folded or collapsed deflection portion can unfurl once in the vessel. The extended deflection portion 482 presents a larger surface area for interfacing with the blood flow, so if oriented appropriately, the tip can be deflected by the flow. The unfurled deflection portion 482 can take on any reasonable shape, including but not limited to the oval shape shown in FIG. 19.

Procedures Using Improved Guidewires

The guidewires described herein can generally be effective for any vascular procedure, but the guidewires are designed to be particularly effective for circuitous vascular paths. Of particular medical importance, procedures in neuro arteries can be useful for the treatment of ischemic stroke conditions, which are caused by vessel blockage, such as due to emboli or thrombus, as well as other procedures in neuro arteries. As noted above, arteries above the carotid arteries tend to have a circuitous path such that access to these vessels can benefit from guidewires effective in circuitous vessels. There is a right carotid artery and a left carotid artery, and as used herein, carotid artery is used synonymously with common carotid artery. Each common carotid artery branches into an internal carotid artery and an external carotid artery, and the internal carotid artery proceeds into the skull. In some embodiments, procedures performed following delivery of the guidewire can be directed, for example, to at least partial removal and/or treatment generally of blockages from the artery.

Figure 20:
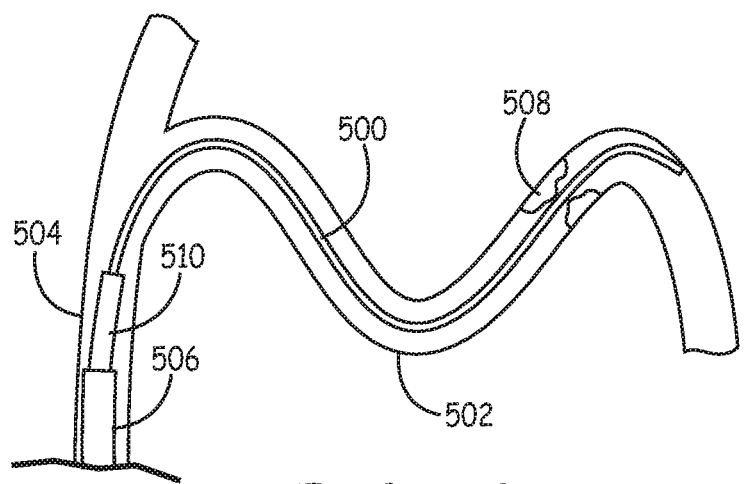
FIG. 20 is a cut away view of a guidewire directed into a circuitous blood vessel from a guide catheter with the distal tip extending past a treatment location.

Referring to a representative use of a guidewire in FIG. 20, the delivery of an improved guidewire 500, such as a guidewire with a hyperbolic taper, is shown delivered into branch vessel 502 from a common vessel 504. Guidewire 500 is optionally delivered from a guide catheter 506 located in common vessel 504. For neuro procedures, a guide catheter can be placed within the carotid artery or other safe vessel at an appropriate location for delivery of a guide catheter, and the guidewire can be tracked past multiple vessel branches once delivered from a guide catheter. As shown in FIG. 20, the distal tip of guidewire 500 is placed in a location past a treatment location 508, which can correspond to an emboli, thrombus, an occlusion, a partial occlusion, or other vessel condition warranting attention with a treatment structure. An ancillary percutaneous device 510 is being shown delivered out from guide catheter 506 for delivery to or near treatment location 508. Ancillary percutaneous device 510 can be, for example, an aspiration catheter, an angioplasty balloon, a stent delivery catheter, microcatheter, or the like. Ancillary percutaneous device 510 can be selected to the performance of a specific procedure or to facilitate delivery of further devices.

Figure 21:
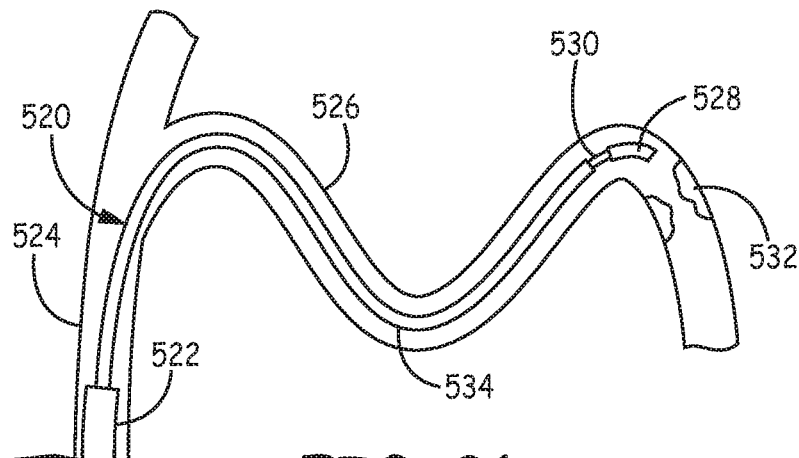
FIG. 21 is a cut away view of an integrated guide structure with an extendable tip positioned in a blood vessel with the tip short of reaching a treatment location.
Figure 22:
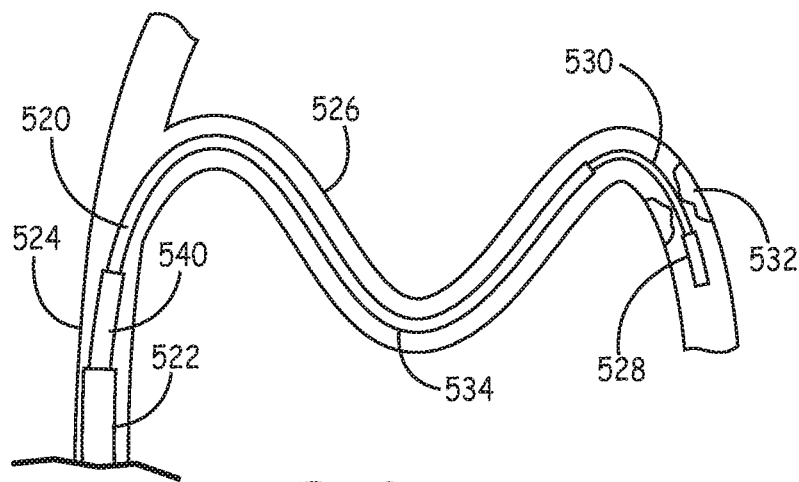
FIG. 22 is a cut away view of the integrated guide structure of FIG. 21 with the tip extended to reach past a treatment location.

A representative use of an extendable guidewire with an integrated guide structure 520 is depicted in FIGS. 21 and 22. Referring to FIG. 21, integrated guide structure 520 is delivered from a guide catheter 522 through a common vessel 524 to a branch vessel 526. As shown in FIG. 21, a tip 528 of corewire 530 of the integrated guide structure 520 is extended as far as comfortable in vessel 526 while still being short of treatment site 532. Referring to FIG. 22, corewire 530 is extended in a distal direction relative to an approximately fixed overtube 534 such that tip 528 extends past treatment site 532, which is comparable to treatment site 508 discussed above. An ancillary percutaneous device 540 comparable with ancillary treatment device 510 is shown in FIG. 22 being delivered from guide catheter 522 on its way to treatment site 532. Thus, the use of an extendable guidewire provides access to treatment site 532 that may be difficult to reach or unreachable otherwise.

Figure 23:
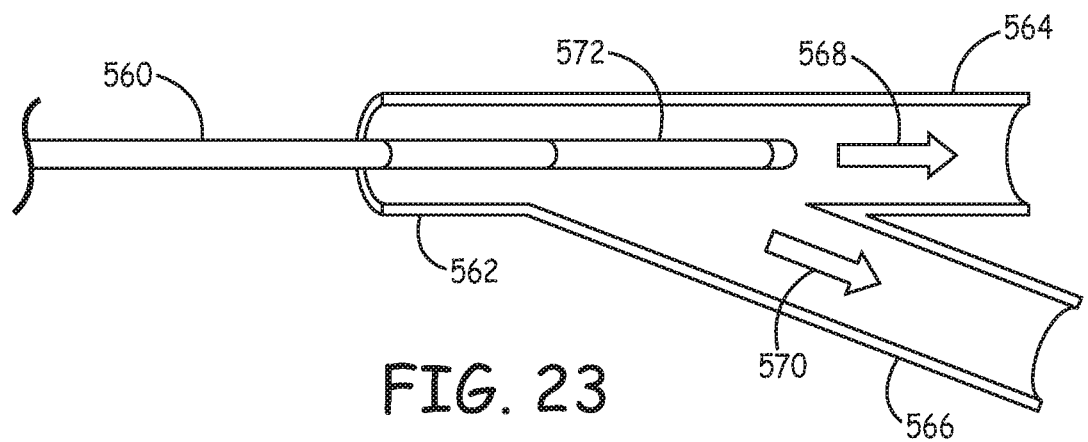
FIG. 23 is a cut away view of a flexible tip guidewire within a blood vessel near a branch with the guidewire oriented to avoid redirection of the tip by the flow.
Figure 24:
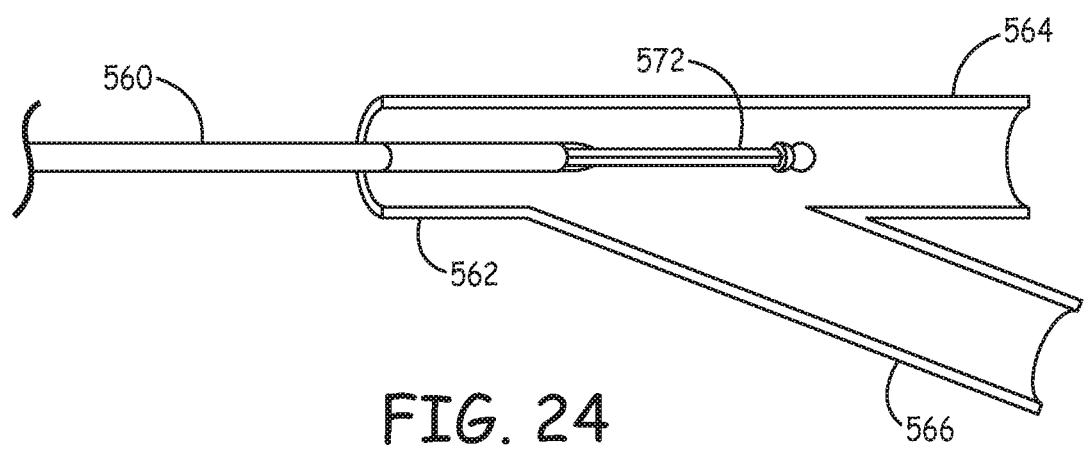
FIG. 24 is a cut away view of the guidewire of FIG. 23 reoriented to provide for influence of the guidewire tip by the flow.
Figure 25:
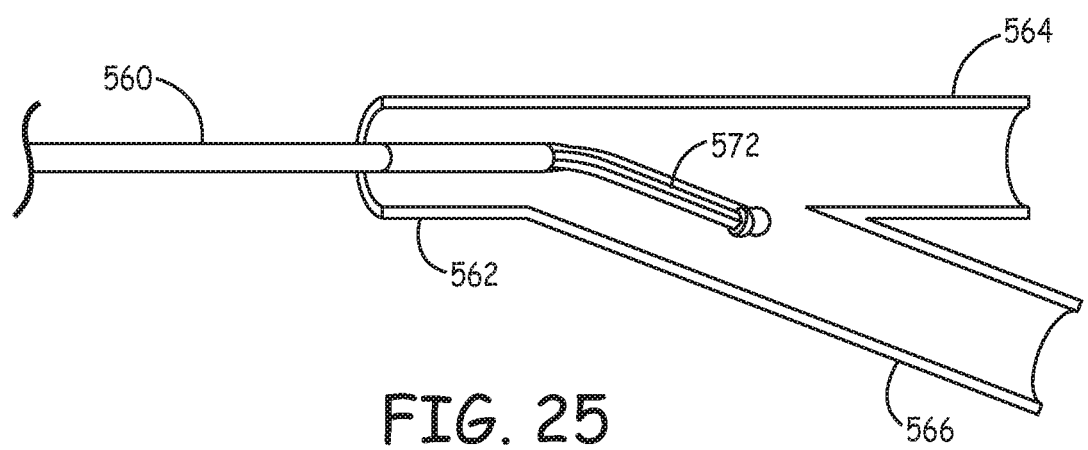
FIG. 25 is a cut away view of the guidewire in the orientation of FIG. 24 in which the tip has been reoriented by the flow to direct the tip toward the lower vessel of the branch.

Use of a flow directed guidewire is shown in FIGS. 23-25. Referring to FIG. 23, guidewire with a flexible polymer, flow directionable, tip 560 is shown in vessel 562 near a branch into vessels 564, 566. The direction of the split flow at the branch is depicted with flow arrows 568, 570. Guidewire 560 is oriented with tip 572 having its flattened surface in the plane of the change in flow direction such that the tip is not redirected by the flow. In this orientation, guidewire 560 can be advanced into vessel 564. Referring to FIG. 24, guidewire 560 is rotated 90 degrees relative to the orientation in FIG. 23. In the orientation of FIG. 24, the plane of the flattened tip is roughly perpendicular to the flow change so that the flexible tip can bend in response to the flow change. If appropriately catching the flow change, tip 572 can be redirected into vessel 566 as shown in FIG. 25. Advancement of guidewire 560 then directs the guidewire into vessel 566.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A guidewire comprising a solid wire of a biocompatible metal, having a length from about 90 cm to about 300 cm, a proximal diameter from about 0.0075 inches (in) to about 0.03 in, and comprising a taper with an approximately hyperbolic tangent shape along a distal third of the guidewire length forming a reduced diameter of the wire, wherein the hyperbolic taper has a length from about 10 cm to about 60 cm.

2. The guidewire of claim 1 wherein the taper reduces the diameter over the length of the taper by about 20% to about 90% of a proximal diameter adjacent the taper.

3. The guidewire of claim 1 further comprising a coil secured over a portion of the taper along the solid wire.

4. The guidewire of claim 3 further comprising a ball weld at a distal end of the wire securing the coil on the wire.

5. The guidewire of claim 3 further comprising a torque stabilizer, a proximal braze securing a proximal end of the coil to the wire or both.

6. The guidewire of claim 3 wherein the coil is stretched.

7. The guidewire of claim 3 wherein the coil has a length from about 1 cm to about 35 cm.

8. The guidewire of claim 3 wherein the coil comprises spring metal.

9. The guidewire of claim 3 wherein the coil is covered with a polymer cover.

10. The guidewire of claim 1 wherein the wire has a length from about 100 cm to about 250 cm, a diameter along the proximal section of the wire from about 0.025 in to about 0.009 in and a diameter at the distal tip of the wire from about 0.0015 in to about 0.006 in.

11. The guidewire of claim 1 wherein the taper has a length from about 20 cm to about 50 cm.

12. The guidewire of claim 1 further comprising a distal tip with a constant diameter and extending from the taper.

13. The guidewire of claim 12 wherein the distal tip has a length from about 0.5 cm to about 10 cm.

\* \* \* \* \*